US010264974B2

(12) United States Patent
Hong et al.

(10) Patent No.: US 10,264,974 B2
(45) Date of Patent: Apr. 23, 2019

(54) HIGH RESOLUTION IMAGING USING NEAR-INFRARED-II FLUORESCENCE

(71) Applicant: The Board of Trustees of the Leland Stanford Junior University, Stanford, CA (US)

(72) Inventors: Guosong Hong, Stanford, CA (US); Jerry Chung-yu Lee, San Diego, CA (US); Ngan Fong Huang, Mountain View, CA (US); John P. Cooke, Stanford, CA (US); Hongjie Dai, Cupertino, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 700 days.

(21) Appl. No.: 14/443,899

(22) PCT Filed: Nov. 20, 2012

(86) PCT No.: PCT/US2012/066157
§ 371 (c)(1),
(2) Date: May 19, 2015

(87) PCT Pub. No.: WO2014/081419
PCT Pub. Date: May 30, 2014

(65) Prior Publication Data
US 2015/0297086 A1    Oct. 22, 2015

(51) Int. Cl.
*A61B 5/00* (2006.01)
*G01N 21/64* (2006.01)
(Continued)

(52) U.S. Cl.
CPC .............. *A61B 5/0071* (2013.01); *A61B 5/00* (2013.01); *A61B 5/0261* (2013.01);
(Continued)

(58) Field of Classification Search
None
See application file for complete search history.

(56) References Cited

U.S. PATENT DOCUMENTS

2005/0020923 A1* 1/2005 Frangioni .......... A61K 49/0017
                                                 600/473
2005/0136258 A1* 6/2005 Nie ................. A61K 47/48861
                                                 428/402
(Continued)

OTHER PUBLICATIONS

Hong, In Vivo Fluorescence Imgaing with AG2S Quantum Dots in teh SEcond Near-Infrared Region, Angew. Chem, Sep. 2012.*
(Continued)

*Primary Examiner* — Tse W Chen
*Assistant Examiner* — Joanne M Hoffman
(74) *Attorney, Agent, or Firm* — Brian E. Davy; Bozicevic, Field & Francis LLP

(57) ABSTRACT

Disclosed are methods for imaging lumen-forming structures such as blood vessels using near-infrared fluorescence in the NIR-II region of 1000-1700 nm. The fluorescence is created by excitation of solubilized nano-structures that are delivered to the structures, such as carbon nanotubes, quantum dots or organic molecular fluorophores attached to hydrophilic polymers. These nanostructures fluoresce in the NIR-II region when illuminated through the skin and tissues. Fine anatomical vessel resolution down to ~30 μm and high temporal resolution up to 5-10 frames per second is obtained for small-vessel imaging with up to 1 cm penetration depth in mouse hind limb, which compares favorably to tomographic imaging modalities such as CT and MRI with much higher spatial and temporal resolution, and compares favorably to scanning microscopic imaging techniques with much deeper penetration.

13 Claims, 19 Drawing Sheets

(51) Int. Cl.
A61K 49/00 (2006.01)
A61B 5/026 (2006.01)
A61B 5/0275 (2006.01)

(52) U.S. Cl.
CPC .......... *A61B 5/0275* (2013.01); *A61B 5/4887* (2013.01); *A61B 5/7278* (2013.01); *A61K 49/0019* (2013.01); *A61K 49/0041* (2013.01); *A61K 49/0054* (2013.01); *A61K 49/0093* (2013.01); *A61K 49/0095* (2013.01); *G01N 21/6428* (2013.01); *G01N 21/6456* (2013.01); *A61B 5/0075* (2013.01); *A61B 5/0086* (2013.01)

(56) References Cited

U.S. PATENT DOCUMENTS

| | | | | |
|---|---|---|---|---|
| 2006/0134002 | A1* | 6/2006 | Lin | A61K 49/0032 424/9.6 |
| 2007/0297988 | A1* | 12/2007 | Wu | A61K 49/0032 424/9.6 |
| 2008/0102036 | A1* | 5/2008 | Poss | A61K 49/0017 424/9.6 |
| 2008/0213189 | A1* | 9/2008 | Lee | A61K 49/0423 424/9.32 |
| 2009/0087493 | A1* | 4/2009 | Dai | A61K 9/0092 424/490 |
| 2009/0098057 | A1* | 4/2009 | Zheng | A61K 49/0032 424/9.6 |
| 2009/0234236 | A1* | 9/2009 | Lomnes | A61B 5/026 600/504 |
| 2009/0304581 | A1 | 12/2009 | Scheinberg et al. | |
| 2012/0049088 | A1* | 3/2012 | Klose | A61B 5/0073 250/459.1 |
| 2012/0323112 | A1* | 12/2012 | Jokerst | A61K 49/225 600/420 |
| 2013/0039848 | A1* | 2/2013 | Bradbury | A61K 49/0019 424/1.37 |

OTHER PUBLICATIONS

Michalet, Single-quantum dot imaging with a photon counting camera, Curr PHarm Biotechnol. Aug. 2009.*
Robinson, "In Vivo Fluorescence Imagining in the NIR-II with Long Circulating Carbon Nanotubes Capable of Ultra-High Tumor Uptake", J Am. Chem. Soc. Jun. 2012, pp. 1-8.*
Zhang, "Ag2S Quantum Dot: A Bright and Biocompatible Fluorescent Nanoprobe in the Second Near-Infrared Window", ACS NANO, Apr. 2012, pp. 3695-3702.*
Bergeron, L., "Stanford researchers use fluorescent nanotubes to illuminate the inner workings of laboratory mice," Stanford Report, May 31, 2011 (http://news.stanford.edu/news/2011/may/nanotubes-imaging-mice-053111.html).
De La Zerda, A., et al., "Ultrahigh Sensitivity Carbon Nanotube Agents for Photoacoustic Molecular Imaging in Living Mice," Nano Lett. (2010) 10:(6):2168-2172.
Hong, G., et al., "Near-Infrared-Fluorescence-Enhanced Molecular Imaging of Live Cells on Gold Substrates," Agnew. Chem, Int. Ed. (2011) 50:4644-4648.
Hong, G., et al., "Multifunctional in vivo vascular imaging using near-infrared II fluorescence," Nature Medicine (2012) 18(12):1841-1846.
Hong, G., et al., "In Vivo Fluorescence Imaging with Ag2S Quantum Dots in the Second Near-Infrared Region," Angew. Chem. Int. Ed. (2012) 124:9956-9959.
Prosposito, P., et al., "Organically modified sol-gel films doped with infrared dyes: an optical investigation," Superficies y Vacio (1999) 9:85-88.
Welsher, K., et al., "A route to brightly fluorescent carbon nanotubes for near-infrared imaging in mice," Nature Nanotechnology (2009) 4(11):773-780.
Welsher, K., et al., "Deep-tissue anatomical imaging of mice using carbon nanotube fluorphores in the second near-infrared window," Proc. Nat. Acad. Sci. (2011) 108(22):8943-8948.
Yuan, T., et al., Class 1A PI3K regulates vessel integrity during development and tumorigenesis,: Proc. Nat. Acad. Sci. (2008) 105(28):9739-9744.

\* cited by examiner

Fig. 1E    Fig. 1F    Fig. 1G
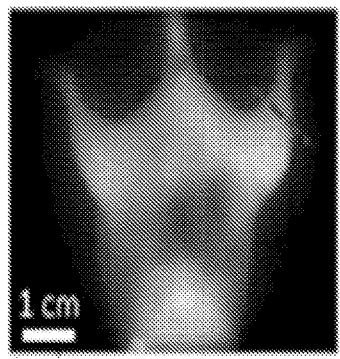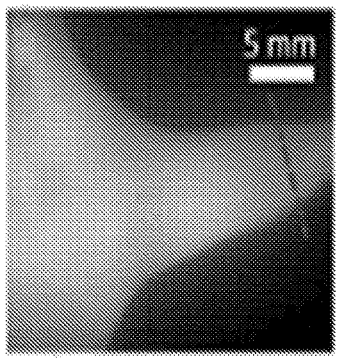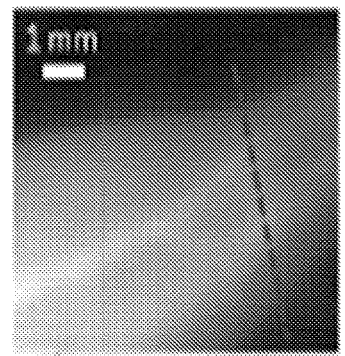
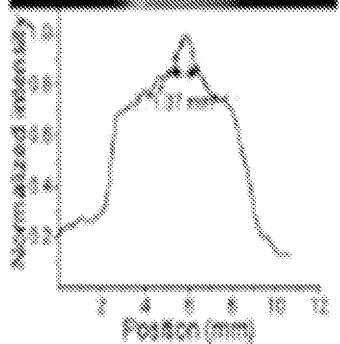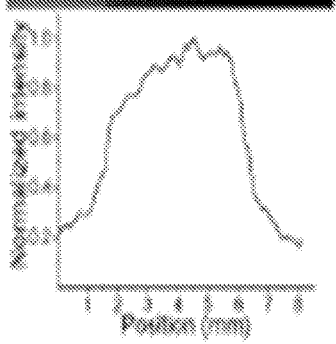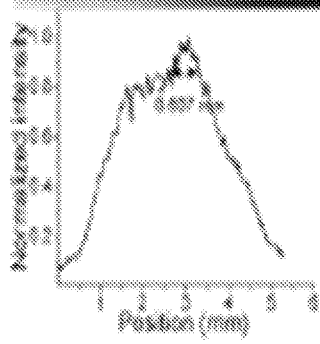

Fig. 1H
Fig. 1I
Fig. 1J
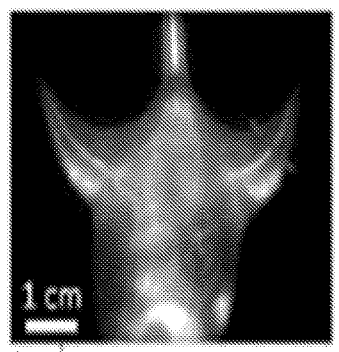
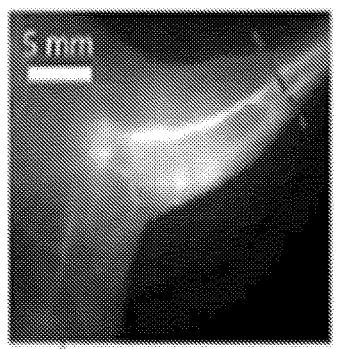
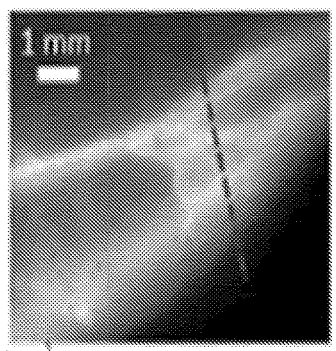
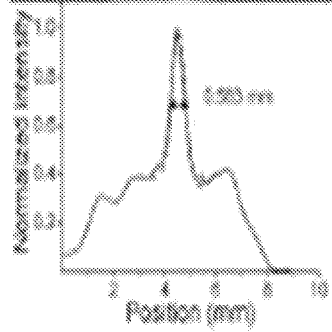
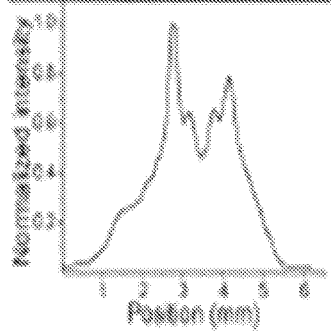
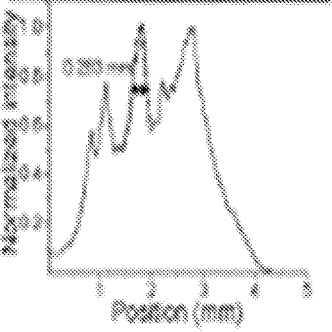

Fig. 2E Scale bar
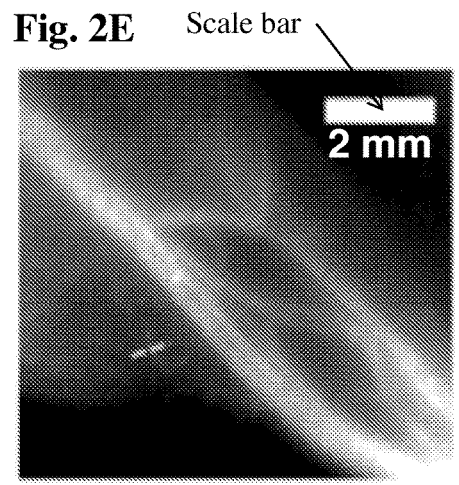
Fig. 2F
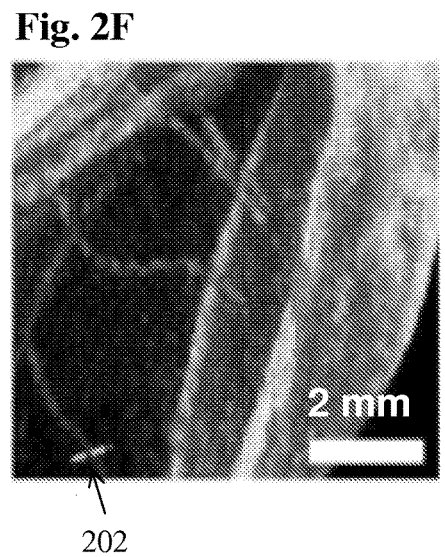
202
Fig. 2G
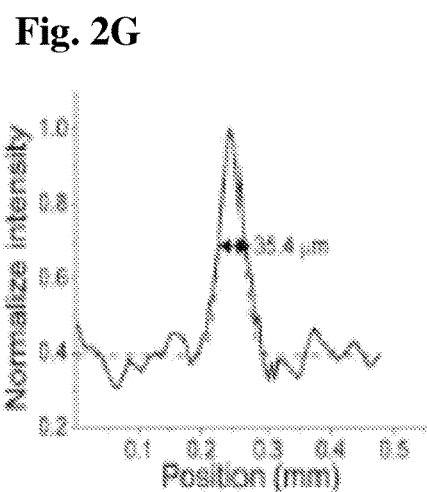
Fig. 2H
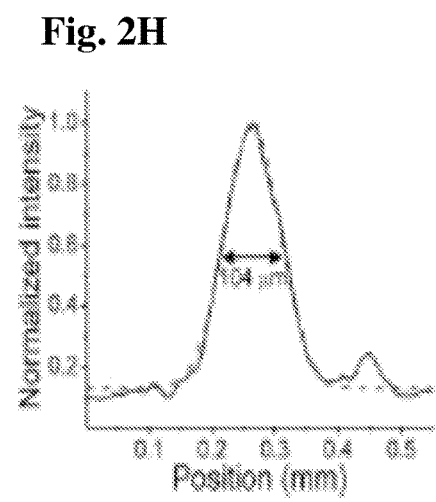

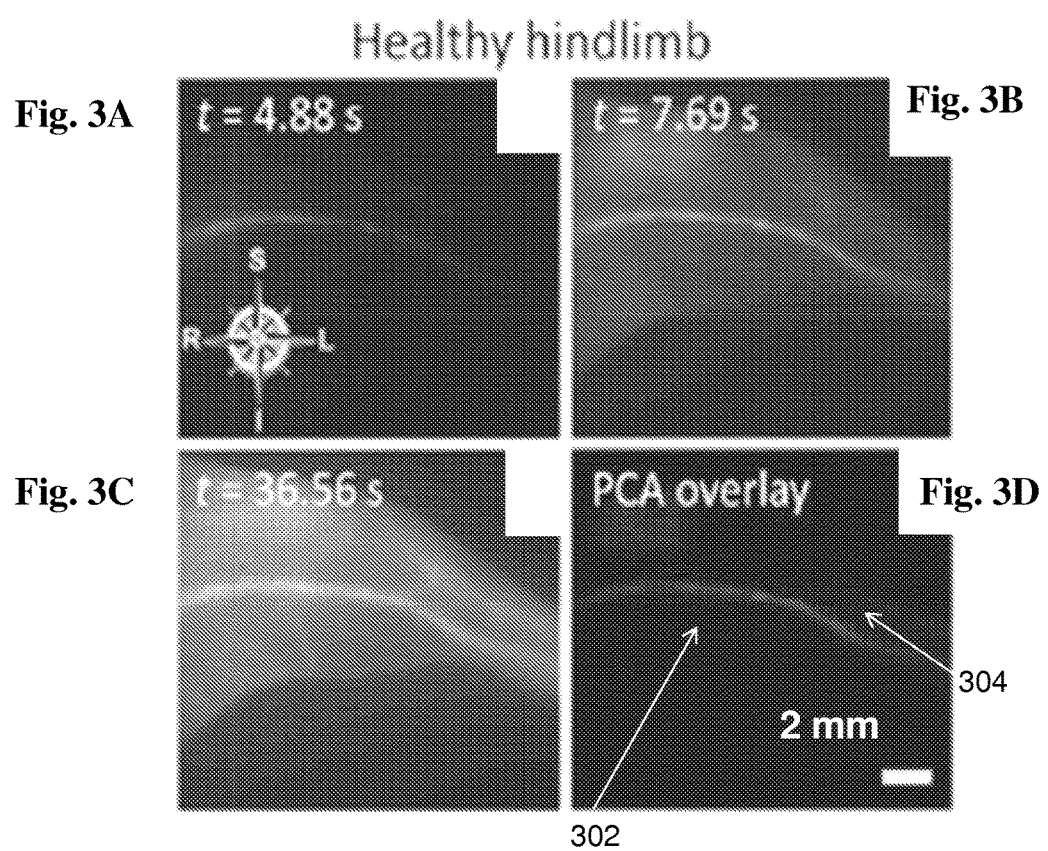

Free IRDye-800    SWNT-PEG-IRDye-800

IC50: 0.1176±0.0237 g/L

PEG coating

HIGH RESOLUTION IMAGING USING NEAR-INFRARED-II FLUORESCENCE

STATEMENT OF GOVERNMENTAL SUPPORT

This invention was made with Government support under contracts HL100397 and HL098688 awarded by the National Institutes of Health. The Government has certain rights in this invention.

CROSS-REFERENCE TO RELATED APPLICATIONS

This application claims priority as the national phase filing of PCT Patent Application No. PCT/US2012/066157 filed on 20 Nov. 2012, the disclosure of which is hereby incorporated by reference in its entirety.

REFERENCE TO SEQUENCE LISTING, COMPUTER PROGRAM, OR COMPACT DISK

None.

BACKGROUND OF THE INVENTION

Field of the Invention

The present invention relates to the field of in vivo fluorescence-based optical imaging of lumen-forming structures such as blood vessels, bile ducts, etc. using near infrared emission in the NIR-II range and further to the use of nanostructures such as carbon nanotubes, quantum dots, etc. solubilized for in vivo use.

Related Art

Presented below is background information on certain aspects of the present invention as they may relate to technical features referred to in the detailed description, but not necessarily described in detail. The discussion below should not be construed as an admission as to the relevance of the information to the claimed invention or the prior art effect of the material described.

Development of new therapies for peripheral arterial diseases (PADs) may be facilitated by imaging that provides anatomic and hemodynamic information with high spatial and temporal resolution. However, current methods for assessing vasculature and hemodynamics in small vessels in vivo are suboptimal. For imaging vascular structures, microscopic computed tomography (micro-CT) and magnetic resonance imaging (MRI) can resolve features down to ~100 μm with deep penetration, but are limited by long scanning and post-processing time and difficulties in assessing vascular hemodynamics. On the other hand, vascular hemodynamics are usually obtained by Doppler measurements of micro-ultrasonography with high temporal resolution of up to 1000 Hz, but spatial resolution attenuates with increased depth of penetration.

In vivo fluorescence-based optical imaging has inherent advantages over tomographic imaging owing to high temporal and spatial resolution. Single-walled carbon nanotubes (SWNTs), nanoscale cylinders of rolled-up graphite sheets comprised of carbon, are an emerging nanomaterial with unique optical properties for in vivo anatomical imaging, tumor detection and photothermal treatment. One unique feature of SWNTs is their intrinsic fluorescence in the second near-infrared (NIR-II, 1.1-1.4 μm) window upon excitation in the traditional near-infrared region (NIR-I, 0.75-0.9 μm) with large Stokes shift up to ~400 nm. Compared to the NIR-I window that has been extensively explored for in vitro and in vivo imaging, the longer wavelength emission in NIR-II makes SWNTs advantageous for imaging owing to reduced photon absorption and scattering by tissues, negligible tissue autofluorescence and thus deeper tissue penetration, allowing for unprecedented fluorescence-based imaging resolution of anatomical features deep to the skin.

Current methodologies for physiological imaging of PADs are suboptimal in that no single modality provides adequate spatial and temporal resolution to accurately assess all critical parameters, i.e. vascular structure, arterial inflow, venous outflow, and tissue perfusion. NIR-II imaging technique simultaneously provides anatomical and hemodynamic information and surpasses the need to use multiple imaging modalities to obtain equivalent data, owing to reduced tissue scattering and deeper anatomical penetration of NIR-II over shorter wavelengths. This is due to the inverse wavelength dependence ($\sim\lambda^{-1.1}$) of photon scattering as they travel through subcutaneous tissue and skin.

In addition, one of the issues of NIR-II imaging remains the limited choices of NIR-II fluorophores such as single-walled carbon nanotubes (SWNTs), certain types of quantum dots (QDs), and a handful of polymethine dyes. Other issues of NIR-II fluorophores include the relatively low fluorescence quantum yields and poor biocompatibility, which limit their use for in vivo imaging with enough temporal resolution. Currently, there is an urgent need for brightly fluorescent and biocompatible NIR-II fluorescent probes for biological imaging both in vitro and in vivo.

SPECIFIC PATENTS AND PUBLICATIONS

Hong et al., "Near-Infrared-Fluorescence-Enhanced Molecular Imaging of Live Cells on Gold Substrates," Agnew. Chem, Int. Ed. 50: 4644-4648 (Apr. 19, 2011), discloses SWNTs coated with DSPE-PEG and conjugated to an IR800 dye and a RGD. Plasmonic gold substrates were used to image cells by near-infrared fluorescence microscopy.

Welsher et al., "Deep-tissue anatomical imaging of mice using carbon nanotube fluorphores in the second near-infrared window," Proc. Nat. Acad. Sci. 108(22): 8943-8948 (May 31, 2011), discloses single-walled carbon nanotubes (SWNT) coated with a PEGylated phospholipid (DSPE-mPEG). These SWNTs were used for imaging lungs and kidneys. Dynamic contrast-enhanced imaging through principal component analysis (PCA) was able to discriminate major organs such as the pancreas. The magnification and spatial resolution used, however, only allowed for imaging major organs in the mouse body. No vessel imaging with artery/vein differentiation or hemodynamic assessment was shown.

Yuan et al., "Class 1A PI3K regulates vessel integrity during development and tumorigenesis," Proc. Nat. Acad. Sci. 105:9739-97-44 (2008) discloses in vivo imaging of mice using an NIR dye-conjugated PEG. NIR fluorophore-conjugated PEG800 was synthesized by conjugation of 20 nmol of N-hydroxysuccinimide ester of IRDye 800. This dye has emission in the NIR-I region (750-900 nm). The vasculature under the skin was imaged with NIR fluorescence excitation light (725-775 nm) with a 795 nm longpass emission filter, not in the NIR-II region (1000-1700 nm).

de la Zerda et al., "Ultrahigh Sensitivity Carbon Nanotube Agents for Photoacoustic Molecular Imaging in Living Mice," Nano Lett., 2010, 10 (6), pp 2168-2172 discloses a novel photoacoustic contrast agent, Indocyanine Green dye-enhanced single walled carbon nanotube (SWNT-ICG).

Scheinberg et al. US PG Pub 2009/0304581, Dec. 10, 2009, entitled "Single wall nanotube constructs and uses therefor," discloses soluble single wall nanotube constructs functionalized with a plurality of a targeting moiety and a plurality of one or more payload molecules. Alternatively, the peptide may be another targeting peptide ligand such as, but not limited to, a cyclic RGD or an NGR peptide that are effective to target endothelial vasculature associated with the cancer. Tumor growth in vivo was assessed histologically on days 2, 3, 5, 7, and 10 by sacrificing mice and examining the morphology, size, vascularization, and encapsulation of the tumor cells in the leg.

BRIEF SUMMARY OF THE INVENTION

The following brief summary is not intended to include all features and aspects of the present invention, nor does it imply that the invention must include all features and aspects discussed in this summary.

In certain aspects, the present invention comprises a method of imaging a lumen-forming structure. The imaging provides detailed information regarding structures within an internal organ in vivo. These lumen-forming structures may be blood vessels, lymph ducts, bile ducts, milk ducts, etc. The subjects studied in vivo may be humans, higher animals, or plants having vasculature. The method addresses problems such as obtaining high resolution images near infrared images of biological structures that are at a depth within the tissue being studied that is beyond the reach of prior art near infrared imaging.

The present vascular (i.e. lumen-forming structure) imaging methods may comprise steps of: (a) delivering to said organ in said subject solubilized nanostructures that fluoresce in a NIR-II region of 1000 to 1700 nm; (b) fluorescently exciting nanostructures from step (a) in a defined area comprising a vessel; (c) collecting NIR-II fluorescence emission from nanostructures excited in step (b); and (d) analyzing said emission to determine at least one of (i) vessel anatomy (ii) differentiation of arterial and venous blood vessels, (iii) organ perfusion, (iv) blood flow velocity, and (v) new vessel formation over time.

Regarding step (d), analyzing the emission, one may conveniently employ a near infrared (NIR) camera in an imaging system. One may determine at least one of (i) vascular anatomy (e.g. external and internal diameters and lumen circumference; tortuosity and bifurcations), (ii) differentiation of arterial and venous vessels, (iii) tissue perfusion (e.g. a qualitative or quantitative assessment of blood flow), (iv) blood flow velocity (i.e. ml/min), and (v) evidence of angiogenesis or arteriogenesis (e.g. new blood vessel formation or vascular remodeling). Blood flow velocity (mL/min) and tissue perfusion (mL/min/mg) are determined by correlating to the increase of NIR-II signal in corresponding vessels and tissues observed in time course as NIR-II reporters (carbon nanotubes or $Ag_2S$ quantum dots) flow through. The present invention provides a way of correlating the NIR-II signal with blood flow and perfusion based on both theoretical simulation and experimental measurements.

In certain aspects, the images obtained are used to determine (iv) blood flow velocity within a defined region in the subject by measuring changes in fluorescent image intensity over time. The analyzing is done by principal component analysis (PCA) of blood flow hemodynamics to assign colors to components of images and differentiate veins versus arteries.

In certain aspects, the solubilized nanostructures may be delivered by intravenous injection, subcutaneous injection, or intramuscular injection.

In certain aspects, the solubilized nanostructure is a carbon nanostructure. The carbon nanostructure may be a SWNT. The solubilized nanostructure may be solubilized with polyethylene glycol (PEG) which is non-covalently attached to the nanostructure.

In certain aspects, the solubilized nanostructure is a quantum dot fluorescing in the NIR-II region. The quantum dot is selected from the group consisting of $Ag_2S$, PbS and $Ag_2Se$. In further aspects, when the quantum dot selected as $Ag_2S$, its diameter is between about 2 and 50 nm. The diameter may be selected for optimum quantum yield, and in some aspects of the present invention may be about 5 nm for highest NIR-II emission.

In certain aspects, the solubilized nanostructures further comprise fluorophores that are organic small molecules fluorescing in the NIR-II region. The organic small molecules may be IR-1051(6-Chlor-2-[2-[3-[(6-chlor-l-ethyl-2H-benzo[cd]indol-2-yliden)-ethyliden]-2-phenyl-1-cyclopenten-l-yl]-ethenyl]-1-ethyl-benzo[cd]indolium tetrafluoroborate), IR-26 (4-(7-(2-phenyl-4H-1-benzothio-pyran-4-ylidene)-4-chloro-3,5-trimethylene-1,3,5-heptatrienyl)-2-phenyl-1-benzothiopyrylium perchlorate), IR-1061 (4-[2-[2-Chloro-3-[(2,6-diphenyl-4H-thiopyran-4-ylidene) ethylidene]-1-cyclohexen-l-yl]ethenyl]-2,6-diphenylthiopyrylium tetrafluoroborate), which may be encapsulated and water-solubilized by bovine serum albumin or other encapsulating supramolecular polymers.

In certain aspects, the present invention concerns a composition comprising an $Ag_2S$ quantum dot linked to branched PEG. The PEG may be linked to an amine-terminated polymer, wherein the amine is coupled to the quantum dot. Each quantum dot may comprise approximately 10 molecules of 6PEG-amine, or 8-12 molecules of 6PEG-amine. 6PEG-amine refers to an amine-terminated branched polyethylene glycol molecule as illustrated in FIG. 7 below.

BRIEF DESCRIPTION OF THE DRAWINGS

FIGS. 1E, 1F and 1G is a series of NIR-I fluorescence images (top) and cross-sectional fluorescence intensity profiles (bottom) along dashed lines of a mouse injected with the SWNT-IRDye-800 conjugates. Gaussian fits to the profiles are shown in dashed curves.

FIGS. 1H, 1I and 1J is a series of NIR-II fluorescence images (top) and cross-sectional fluorescence intensity profiles (bottom) along dashed lines of a mouse injected with the SWNT-IRDye-800 conjugates. Gaussian fits to the profiles are shown in dashed curves.

FIG. 2A is a NIR-II SWNT fluorescence image of a mouse thigh. FIG. 2B is a micro-CT image showing the same area of the thigh as in 2A.

FIG. 2C is a cross-sectional fluorescence intensity profile measured along the dashed bar in 2A with its two peaks fitted to Gaussian functions. FIG. 2D is a cross-sectional intensity profile measured along the dashed lines in 2B with its two peaks fitted to Gaussian functions.

FIGS. 2E, 2F, 2G and 2H is a series of images showing NIR-II fluorescence and micro-CT imaging in the vicinity of the gastrocnemius (calf muscle). FIG. 2E is an NIR-II image at the level of the gastrocnemius. FIG. 2F is a micro-CT image showing the same area of the limb as in 2E. FIG. 2G is a cross-sectional fluorescence intensity profile measured along the dashed lines in 2E with its peak fitted to a Gaussian function. FIG. 2H is a cross-sectional intensity profile measured along the dashed bar 202 in 2F with its peak fitted to a Gaussian function. All scale bars indicate 2 mm.

FIGS. 3A, 3B, 3C, and 3D is a set of images (labeled a, b, c, d, respectively, in the image) showing differentiation of femoral artery from vein in normal and ischemic mice by NIR-II imaging. (3A, 3B, 3C) Time course NIR-II fluorescence images of hindlimb blood flow in a control healthy animal. (3D) PCA overlaid image based on the first 200 frames (37.5 s post injection) of the control animal, where arteries and veins are shown. In the original image, the line indicated by 302 showed a red line, representing an artery; a separate line (shown by arrow 304) representing a vein was in blue.

FIG. 4A is a graph showing the distance travelled by the flow front versus time. FIG. 4B is a graph showing the normalized NIR-II signal in the femoral artery versus time. FIG. 4C is graph showing the linear correlation between the artery blood velocity and NIR-II fluorescence increase in femoral artery.

DETAILED DESCRIPTION OF THE PREFERRED EMBODIMENT

Overview

Figure 1A:
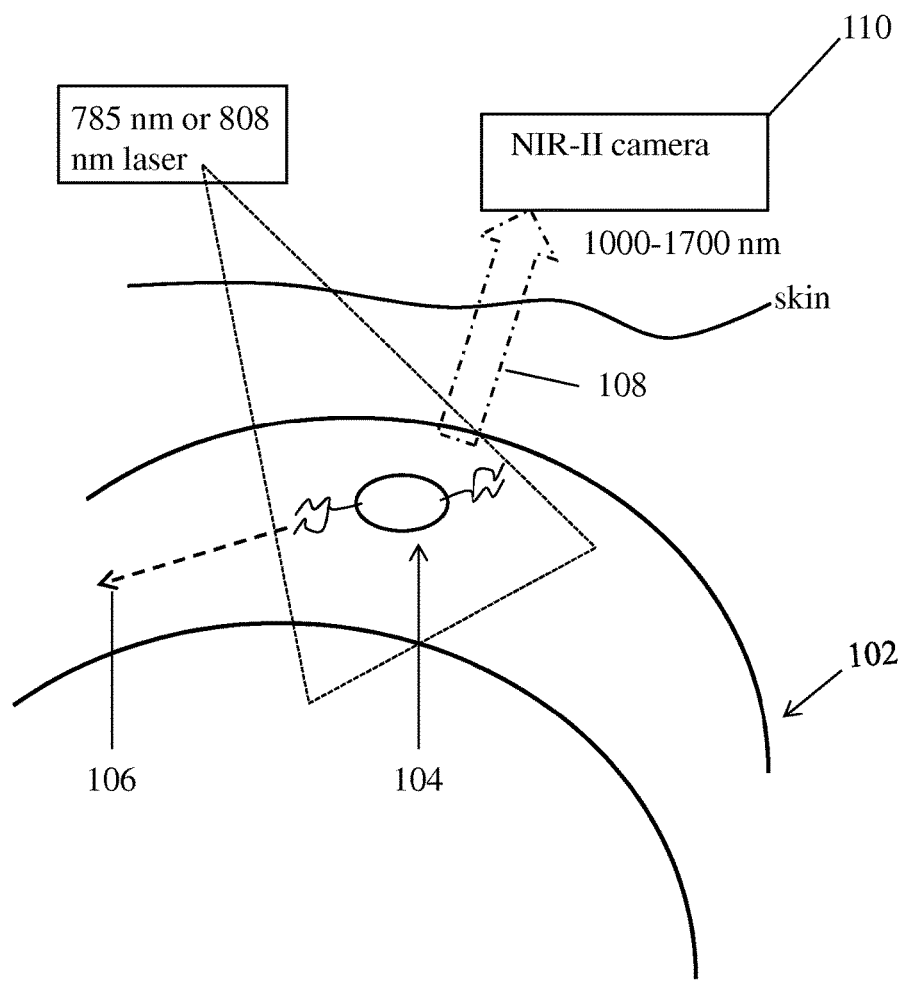
FIG. 1A is a schematic showing excitation and NIR-II emission from a nanoparticle in a lumen-forming structure such as a blood vessel.

Described herein are nanoscale materials suitable for all-optical in vivo imaging on the basis of second near-infrared (NIR-II, 1000-1700 nm) fluorescence and their use in time-resolved imaging of moving tissue such as blood with deep tissue penetration (1-10 mm). The nanoscale materials used include carbon nanotubes (single-walled carbon nanotubes, "SWNTs"), so-called "quantum dots", and polymethine organic dyes encapsulated inside nanoscale proteins or supramolecular polymers, as described further below. These materials are solubilized for injection by a hydrophilic polymer attached to the nanostructure. Owing to the much longer fluorescence emission of NIR-II than traditional NIR (750-1000 nm) and visible fluorescence emission (400-750 nm), these nanomaterials can be used as in vivo fluorescence reporters with much reduced scattering and autofluorescence interference, and can provide deeper tissue penetration depth than traditional optical imaging techniques. The materials are used for epifluorescent imaging, as shown in FIG. 1A. Solubilization of the present nanostructures should be compatible with in vivo use and may be accomplished by polyethylene glycol-phospholipid, or other molecules that have a hydrophobic and a hydrophilic portion, e.g. pyrene-water-soluble metalloporphyrins.

As shown in FIG. 1A, a light source such as a near infrared laser (785 nm or 808 nm laser) irradiates a blood vessel 102 in which a solubilized nanostructure 104 is moving in the bloodstream in the direction of arrow 106. The solubilized nanostructure 104 emits light 108 which is detected by camera 110. Radiation from the laser and the resulting fluorescent emission 108 both pass through the skin with reduced scattering, which is a benefit of using NIR-II emission; as described below, the present methods and system take advantage of the NIR-II window of the electromagnetic spectrum, at about 1000-1700 nm, to accomplish this imaging with deep tissue and skin penetration. Furthermore, the camera 110 is designed to acquire images at video rate over a period of time that allows determinations to be made regarding blood velocity. The camera is preferably connected to a computer for storing image data and deriving blood flow parameters from a sequence of images.

As described in detail below, in vivo real-time epifluorescence imaging of mouse hindlimb vasculatures in the second near-infrared region (NIR-II, 1.0-1.7 μm) was performed using single-walled carbon nanotubes (SWNTs) as fluorophores. Both high spatial (~30 μm) and temporal (<200 ms per frame) resolution for small-vessel imaging with 1-3 mm depth are achieved in the hind limb tissue, which compares favorably to tomographic imaging modalities such as CT and MRI with much higher spatial and temporal resolution, and compares favorably to scanning microscopic imaging techniques with much deeper penetration. Arterial and venous vessels can also be discriminated using a dynamic contrast-enhanced NIR-II imaging technique on the basis of their distinct hemodynamics. Further, precise quantifications of blood velocity in both normal and ischemic femoral arteries with large dynamic range can be achieved using real-time NIR-II imaging method, which is unattainable by ultrasonography at lower blood velocities.

As further described below, quantum dots with bright near-infrared-II (NIR-II, 1000-1700 nm) fluorescence emission at ~1200 nm and six-arm branched PEG surface coating were synthesized for in vivo small animal imaging. The 6PEG-$Ag_2S$ QDs contained no Cd or Pb, minimizing toxicity concerns for in vivo use. In vivo fluorescence imaging in the NIR-II optical window was performed for the first time with QDs. Video-rate dynamic contrast-enhanced imaging revealed deep inner organs and tumor in mice. Due to ultralow background and reduced photon scattering in NIR-II, early-stage detection of ultrasmall tumor (~0.1 $mm^3$) and hindlimb vessel imaging with $Ag_2S$ QDs at high spatial resolution and deep tissue penetration were demonstrated. The 6PEG-$Ag_2S$ QDs afforded an unusually high tumor uptake of QDs of ~10% injected dose/gram, owing to a long circulation half-life of ~4 h. Clearance of the injected 6PEG-$Ag_2S$ QDs occurred mainly through the biliary pathway in mice. The Cd- and Pd-free nature, NIR-II emission, branched PEG coating and favorable pharmacokinetics of 6PEG-$Ag_2S$ QDs make them a promising in vivo imaging agent.

While the examples below are specifically directed to imaging blood vessels, the present methods and materials may also be applied to other types of vascular imaging. The present methods allow for greater depth of imaging, resolution of detail and temporal resolution. As such, they may be applied to imaging of vasculature such as lymph ducts (thoracic duct, trunks and tributaries), bile ducts, lactiferous ducts, pancreatic ducts, ejaculatory ducts, nephritic ducts, subarachnoid space, etc. The solubilized nanostructures are delivered either directly to the vasculature of choice or to a connecting region. As will be understood from the following description, the vasculature being studied will be within a living subject, and therefore will be part of an organ. The image obtained from use of the present methods and materials will therefore ordinarily comprise imaging at least part of an organ. A blood vessel or other vessel is considered an organ, in that an organ is considered to be a part of the body exercising a specific function and composed of different types of tissues. By way of further example, a bile duct is part of the biliary system, which consists of the organs and ducts (bile ducts, gallbladder, and associated structures) that are involved in the production and transportation of bile.

The present methods and materials allow for NIR imaging with high spatial resolution. This may be allow for resolution of, for example, less than 100 μm less than 75 μm, less than 50 μm, less than 30 μm, or less than 10 μm.

The present methods and materials also provide high temporal resolution. That is, the NIR II images are obtained with a short exposure time that allows for multiple successive images to be captured, e.g. by a CCD camera. In the case of rapid movement, this would reduce blurring. This also allows for measurement of temporal changes in an image. The present system can provide a temporal resolution of for example, less than 500 msec (milliseconds) per frame, less than 300 msec per frame, less than 200 msec per frame, less than 50 msec per frame, etc. For example, at less than 200 msec/frame, a new image is taken every 200 milliseconds.

EXAMPLES 1-4

Described in these examples is the use of biocompatible, brightly fluorescent SWNTs as NIR-II imaging agents. They are shown to be suitable for imaging vascular structures down to ~30 μm in mouse hindlimb using an epifluorescence imaging method with an indium-gallium-arsenide (InGaAs) imaging system. Compared to micro-CT, NIR-II fluorescence imaging attains a ~3-fold improvement in spatial resolution. Further, NIR-II imaging allows for differentiation of arteries from veins through principal component analysis (PCA) to obtain dynamic contrast-enhanced imaging. This method can also quantify femoral artery blood flows in both normal and ischemic hindlimbs, and reveal the degree of occlusion due to ischemia. Thus, a single NIR-II imaging modality enables multi-functional imaging capable of accomplishing what is typically done by several traditional techniques including micro-CT, ultrasonography and MRI, making it a unique method that incorporates many desirable features such as high spatial resolution (~30 μm), fast acquisition (<200 ms), good tissue penetration (1-3 mm), vessel specification and blood flow quantification.

NIR-II imaging as used herein compared favorably to micro-CT. Even with voxel (volumetric pixel) dimensions of 40 μm, micro-CT was only capable of resolving vessels of ~100 μm, while NIR-II could distinguish vessels ~3×smaller, without obvious background signal from soft tissue. In terms of imaging depth, NIR-II can achieve a penetration depth of >5 mm in vivo without losing fidelity, whereas micro-CT is able to reconstruct the whole-body structure in 3D owing to the unlimited penetration of X-rays. The time required for micro-CT (hours) as opposed to NIR-II imaging (sub-second) also means longer anesthesia time and high radiation doses, carrying risks of nephrotoxicity, anaphylaxis, and tissue injury.

NIR-II imaging has three salient advantages over ultrasonography. First, NIR-II is able to image smaller vessels. Even with a high frequency (40 MHz) transducer, the diameter of mouse vessels could not be accurately determined with ultrasound, due to poor spatial resolution and low contrast. Second, NIR-II imaging is able to resolve both arterial and venous vessels anatomically and hemodynamically using PCA. Third, NIR-II imaging can be used to acquire hemodynamic data in conditions of reduced flow (e.g., ischemic hindlimb), below the detection limit of ultrasonography.

Due to the many benefits of NIR-II fluorescence imaging over other pre-clinical imaging modalities, this dual-modality method may be useful in a variety of cardiovascular models.

Although the examples below focus on assessing blood flow of small vessels, NIR-II imaging could be used to characterize in vivo the degree of stenosis or aneurysmal dilation of vessels. Because of its temporal resolution, it might also be useful for imaging dynamic changes in vessel diameter due to active vasodilation or vasoconstriction. It is conceivable that NIR-II fluorescence imaging with SWNTs and other novel NIR-II fluorophores including quantum dots and synthetic organic dyes could lead to many translational and clinical applications.

EXAMPLES 5-9

These examples describe the use of a new NIR-II fluorophore, silver sulfide ($Ag_2S$) QDs for imaging xenograft tumors and vascular structures with high fluorescence quantum yield (15.5%) of NIR-II emission at ~1200 nm. The present QDs are free of heavy metals of Cd, Hg or Pb, and can be used to detect small tumors down to ~0.1 $mm^3$ and distinguish arterial and venous hindlimb vessels with ~2 mm depth of penetration Definitions Unless defined otherwise, all technical and scientific terms used herein have the same meaning as commonly understood by those of ordinary skill in the art to which this invention belongs. Although methods and materials similar or equivalent to those described herein can be used in the practice or testing of the present invention, the preferred methods and materials are described. Generally, nomenclatures utilized in connection with, and techniques of, cell and molecular biology and chemistry are those well known and commonly used in the art. Certain experimental techniques, not specifically defined, are generally performed according to conventional methods well known in the art and as described in various general and more specific references that are cited and discussed throughout the present specification. For purposes of clarity, the following terms are defined below.

Ranges: For conciseness, any range set forth is intended to include any sub-range within the stated range, unless otherwise stated. A sub-range is to be included within a range even though no sub-range is explicitly stated in connection with the range. As a non-limiting example, a range of 120 to 250 includes a range of 120-121, 120-130, 200-225, 121-250 etc. The term "about" has its ordinary meaning of approximately and may be determined in context by experimental variability. In case of doubt, "about" means plus or minus 5% of a stated numerical value.

The term "carbon nanotube" means a nanostructure comprising a sheet of graphene rolled into a cylinder as small as 1 nm in diameter. Single-walled nanotubes (SWNTs) have been synthesized. The electronic properties of a nanotube depend on the angle (chirality) with which it is rolled up—the present nanotubes can be metals, small-gap semiconductors, or large-gap semiconductors. Carbon nanotubes may include other materials. Metallic tubes have shown ballistic conduction on length scales of a micron or more. Nanotubes are also the stiffest known material, with a Young's modulus of ~1 TPa, which makes them excellent candidates for nanomechanical systems. Carbon nanotubes, as used herein, includes structures that are not entirely carbon, such as BCN nanotubes. The term "carbon nanotube" is intended to include equivalent structures having graphene in other forms. This includes a single sheet of graphene formed into a sphere, which constitutes a carbon nanosphere, commonly referred to as a buckyball or fullerene. This also includes nanohorns and onions, as described e.g. in US 20110262340, "Production of Carbon nanostructures from Functionalized Fullerenes." The present nanotubes may contain other atoms or dopants, such as silicon, etc.

The term "fullerene" refers to a material including a set of carbon cage molecules. For certain implementations, a fullerene molecule can include a three dimensional skeleton that includes multiple carbon atoms, and that forms a closed shell, which can be spherical or semi-spherical in shape. Carbon atoms of a fullerene molecule typically are bonded to three nearest-neighbors arranged in a tetrahedral geometry. A fullerene molecule can be designated as C "n" where n is an integer corresponding to the number of carbon atoms included in a carbon skeleton of the fullerene molecule. For example, C60 refers to a truncated icosahedron molecule with 60 carbon atoms including 32 faces, of which 12 are substantially pentagonal and 20 are substantially hexagonal. Other examples of fullerene molecules include Cn where n is in the range of 50 to 250, such as C70, C72, C74, C76, C78, C80, C82, and C84. The term "fullerene derivative" refers to a fullerene that has been modified in any manner, including charged, hetero, or substituted forms thereof.

The term "PEG" means polyethylene glycol, a polymer with the structure (—$CH_2CH_2O$—)n that is synthesized normally by ring opening polymerization of ethylene oxide. The PEG used herein will impart water (and serum) solubility to the hydrophobic nanostructure and lipid portion of the polar lipid. The polymer is usually linear at molecular weights (MWs) ≤10 kD. The PEG used here will have an MW around 5,400, preferably above 2,000, or about 45 repeating ethylene oxide units. However, the higher MW PEGs (higher "n" repeating units) may have some degree of branching. Polyethylene glycols of different MWs have already been used in pharmaceutical products for different reasons (e.g., increase in solubility of drugs). Therefore, from the regulatory standpoint, they are very attractive for further development as drug or protein carriers. The PEG used here should be attached to the nanostructures at a density adjusted for the PEG length. For example, with PL-PEG 2000, we have an estimate of ~4 nm spacing between PEG chain along the tube.

Figure 7:
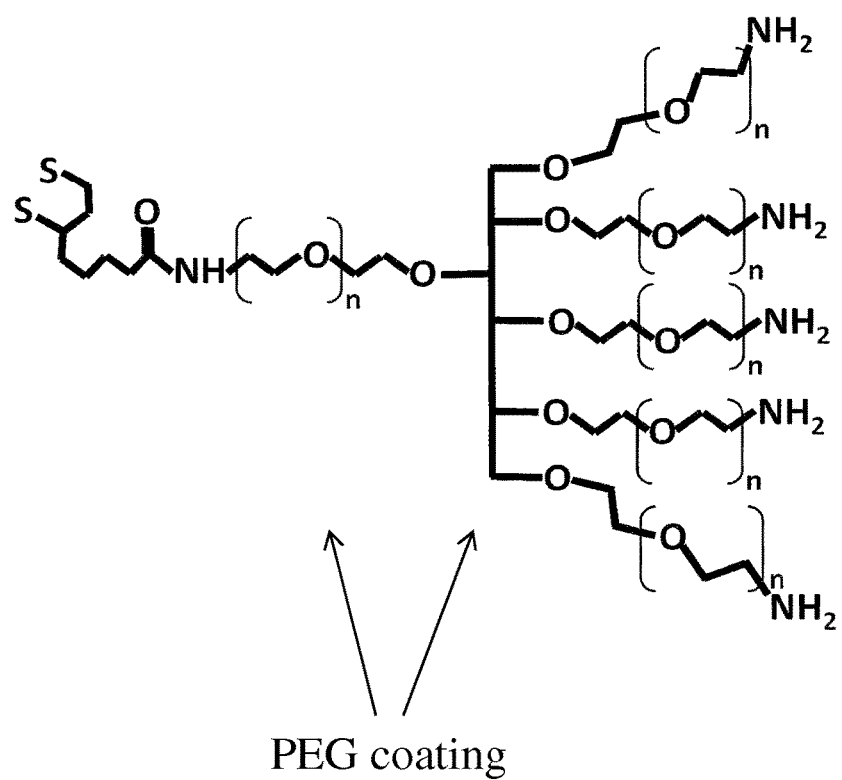
FIG. 7 is a diagram that illustrates the structure of a polyethylene glycol (PEG) molecule comprised in the coating applied to the quantum dot shown in FIG. 6. The "n" subscript indicates that there are a number of repeating ethylene oxide monomer units in each of the six chains drawn. In this example, n=38 for each chain, while all six chains have the same n value.

The term "6PEG-amine" means a PEG derivative that has been functionalized with an amine terminus and has 6 PEG arms. An example of 6PEG-amine is illustrated in FIG. 7. It is further described in, for example, Nho et al. US 6,858,736, issued Feb. 22, 2005.

The term "principal component analysis" or PCA refers to a mathematical procedure that uses an orthogonal transformation to convert a set of observations of possibly correlated variables into a set of linearly uncorrelated variables called principal components. It can be used in an imaging method as reported in Hillman et al., "All-optical anatomical co-registration for molecular imaging of small animals using dynamic contrast," Nature Photonics 1:526-530 (2007) and Welsher et al Proc. Nat. Acad. Sci., cited above. The technique as applied here uses a time series of images acquired after injection of an inert dye. Differences in the dye's in vivo biodistribution dynamics allow precise delineation and identification of major organs. Such co-registered anatomical maps permit longitudinal organ identification irrespective of repositioning or weight gain, thereby promising greatly improved accuracy and versatility for studies of orthotopic disease, diagnostics and therapies.

The term "phospholipid" means a molecule having an aliphatic carbon chain with a terminal phosphate group. Typically the phospholipids will comprise a glycerol backbone, attached to two fatty acid (aliphatic groups) esters and an alkyl phosphate. Suitable phospholipids for use in this invention include, without limitation, dimyristoyl phosphatidylcholine, distearoyl phosphatidylcholine, dilinoleoyl-phosphatidylcholine (DLL-PC), dipalmitoyl-phosphatidyl-choline (DPPC), soy phophatidylchloine (Soy-PC or PCs) and egg phosphatidycholine (Egg-PC or PCE). Suitable phospholipids also include, without limitation, dipalmitoyl phosphatidylcholine, phosphatidyl choline, or a mixture thereof. Exemplified below is use of the phospholipid 1,2-distearoyl-sn-glycero-3-phosphoethanolamine coupled to PEG.

The term "nanostructure" refers to a discrete particle having a defined structure and dimensions on the order of about 0.2 nm to about 10 nm in size (nanoscale), which is between molecular (0.01~0.1 nm) and microscopic structures (~μm). If any one of the three dimensions of a certain structure lies in the nanoscale, it can be referred to as a nanostructure. For example, semiconducting quantum dots are 3D nanostructures, carbon nanotubes are 2D nanostructures, while single graphene sheets are 1D nanostructures. In terms of the chemical composition, the defined structure may be a macromolecule (carbon nanotube) or a crystalline structure ($Ag_2S$ quantum dots, fullerenes). Examples of nanostructures include quantum dots, carbon nanotubes, silicon nanowires, Cn fullerenes, etc.

The term "quantum dot" or "QD" refers to a nanoscale material (on the order of 2-10 nm, preferably in the range of 5-6 nm) whose excitons are confined in all three spatial dimensions. Consequently, such materials have electronic properties intermediate between those of bulk semiconductors and those of discrete molecules. Quantum dots are semiconductors whose electronic characteristics are closely related to the size and shape of the individual crystal. Generally, the smaller the size of the crystal, the larger the band gap, the greater the difference in energy between the highest valence band and the lowest conduction band becomes, therefore more energy is needed to excite the dot, and concurrently, more energy is released when the crystal returns to its resting state. For example, in fluorescent dye applications, this equates to higher frequencies of light emitted after excitation of the dot as the crystal size grows smaller, resulting in a color shift from red to blue in the light emitted.

The quantum dots of the present invention will have fluorescence in the NIR-II range. The present quantum dots include one quantum dot or a plurality of quantum dots. Quantum dots are typically very small semiconductors, having dimensions in the nanometer range. Because of their small size, quantum dots may exhibit quantum behavior that is distinct from what would otherwise be expected from a larger sample of the material. In some cases, quantum dots may be considered as being crystals composed of materials from Groups TI-VI, III-V, or IV-VI materials. The quantum dots employed herein may be formed using any appropriate technique. Examples of specific pairs of materials for forming quantum dots include, but are not limited to, MgO, MgS, MgSe, MgTe, CaO, CaS, CaSe, CaTe, SrO, SrS, SrSe, SrTe, BaO, BaS, BaSe, BaTe, ZnO, ZnS, ZnSe, ZnTe, HgO, HgS, HgSe, HgTe, $Al_2O_3$, $Al_2S_3$, $Al_2Se_3$, $Al_2Te_3$, $Ga_2O_3$, $Ga_2S_3$, $Ga_2Se_3$, $Ga_2Te_3$, $In_2O_3$, $In_2S_3$, $In_2Se_3In_2Te_3$, $SiO_2$, $GeO_2$, $SnO_2$, SnS, SnSe, SnTe, PbO, $PbO_2$, PbS, PbSe, PbTe, AlN, AlP, AlAs, AlSb, GaN, GaP, GaAs, GaSb, InN, InP, InAs and InSb. Additional examples of quantum dot materials include $CuInSe_2$, $CuS_2$, and $AgS_2$, described below. Because of the present in vivo application, the present quantum dots should be non-toxic, i.e. cadmium- and lead-free. As described below, in terms of minimum toxicity, preferred materials include $Ag_2S$ and SiP; in terms of optimum emission wavelengths to afford deep body penetration, quantum dots with NIR-II emission (1000-1700 nm) are preferred.

In particular, the term "$Ag_2S$" refers to silver sulfide. An $Ag_2S$ quantum dot is a direct band semiconductor with a bulk band gap energy of about 0.9eV (~1370 nm). Spherical $Ag_2S$ quantum dots with diameters between 5 nm and 10nm can be used for NIR-II imaging applications. While diameter does not show any effect on emission wavelength (~1200 nm in NIR-II), it does play an important role in the fluorescence quantum yield (optimum size is ~5 nm for highest NIR-II emission).

The term "NIR" means near infrared, particularly in the sense of NIR fluorescence. The term also means the near infrared region of the electromagnetic spectrum (from 0.75 to 3 μm). For purposes of biological imaging, the NIR range is divided into NIR-I, around 800 nm (0.75-0.9 μm) and NIR-II, between about 1.0 and 1.7 μm. Specifically, as used herein, the term "NIR-II" refers to the region between about 1000 nm and 1700 nm.

The term "spatial resolution" refers to a feature of image resolution in which two features can be distinguished as separate. This may be considered a measure of how closely lines can be resolved in an image. It depends on properties of the system creating the image. In digital imaging, spatial resolution refers to the number of independent pixel values per unit length. Thus, for example, a spatial resolution of 50 µm means that two fluorescent nanoparticles or groups of particles would appear as separate even though they were only 50 µm apart.

The term "temporal resolution" refers to the duration of time for acquisition of a single frame of a dynamic process, i.e., cine imaging. The time gap between consecutive images indicates the temporal resolution which is given by the formula:

VPS.TR where

VPS=views per segment—a user-defined variable and
TR=time to repetition.

So, for example if the TR is 10 ms and there are 5 views per segment, the temporal resolution would be 50 ms/frame.

The term "lumen-forming structure" means a biological structure that is formed into a lumen for carrying a fluid. As is understood in the art, the lumen is the open inner space or cavity of a tubular organ. Typical lumen-forming structures range in size from 5-10 micrometers in diameter (capillaries) to arteries (aorta, 2.5-3 cm in diameter). They are typically formed from soft tissue such as muscle and connective tissue.

Preparation of Water Soluble SWNT-IRDye-800 Bioconjugate

The preparation of water soluble and biocompatible SWNTs can be found in detail in other publications by an inventor herein, such as US 2009/0166560, "Sensing of biological molecules using carbon nanotubes as optical labels". In general, raw HiPCO SWNTs (high pressure CO conversion, obtained from Unidym Inc, Sunnyvale Calif.) were suspended in 1 wt % sodium deoxycholate aqueous solution by 1 hour of bath sonication. This suspension was ultracentrifuged at 300,000 g to remove the bundles and other large aggregates, the supernatant was retained and 0.75 mg·ml$^{-1}$ of DSPE-mPEG(5 kDa) (1,2-distearoyl-sn-glycero-3-phosphoethanolamine-N-[methoxy(polyethyleneglycol, 5000)], Laysan Bio Inc., Arab, Ala.) along with 0.25 mg·ml$^{-1}$ of DSPE-PEG(5 kDa)-NH$_2$ (1,2-distearoyl-sn-glycero-3-phosphoethanolamine-N-[amino(polyethyleneglycol, 5000)], Sunbright) was added. The resulting suspension was sonicated briefly for 5 min and then dialyzed at pH 7.4 in a 3500 Da membrane (Fisher) with a minimum of six water changes and a minimum of two hours between water changes. To remove aggregates, the suspension was ultracentrifuged again for 1 hour at 300,000 g. This surfactant-exchanged SWNT sample has lengths ranging from 100 nm up to 2.0 µm with the average length of ~500 nm. These amino-functionalized SWNTs were further conjugated with IRDye-800 dye molecule according to the protocol that has been used in our group. Briefly, an SWNT solution with amine functionality at 300 nM after removal of excess surfactant was mixed with 0.1 mM IRDye-800 NHS ester (LI-COR) in PBS at pH 7.4. The reaction was allowed to proceed for 1 h before purification to remove excess IRDye-800 by filtration through 100-kDa filters. The as-made SWNT-IRDye-800 conjugate solution was kept at 4° C. and away from light to avoid photobleaching of IRDye-800 fluorescence.

Figure 5A:
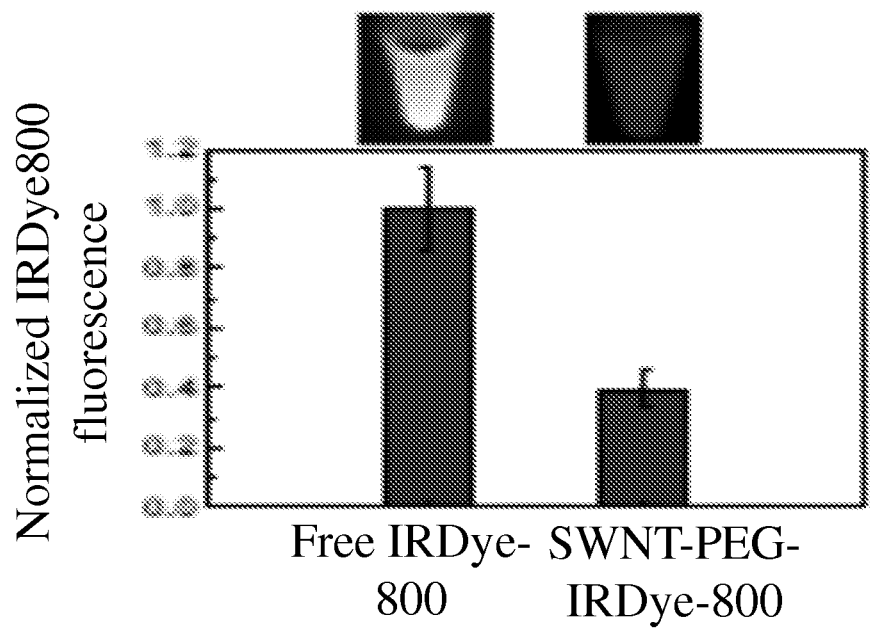
FIG. 5A is a photograph and graph showing normalized IRDye-800 fluorescence for free IRDye-800 and SWNT-PEG-IRDye-800 at the same concentration of IRDye-800, suggesting the photoluminescence of IRDye-800 was quenched by ~60% due to the attachment to SWNTs through the PEG-chains. Inset pictures on top are corresponding photoluminescence images taken in the NIR-I window.
Figure 5B:
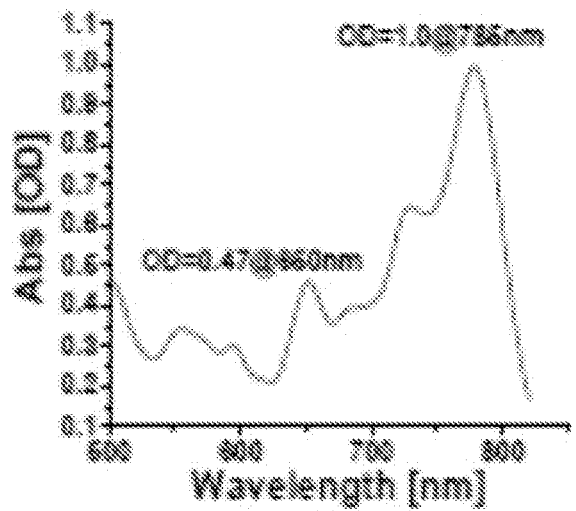
FIG. 5B is a graph showing UV-Vis-NIR absorption spectrum of SWNT-PEG-IRDye-800 conjugate taken in a 1 mm cuvette, where the OD values at 650 nm and 785 nm are used for calculating the average number of SWNT and IRDye-800 molecules in SWNT-PEG-IRDye-800 conjugate
Figure 5C:
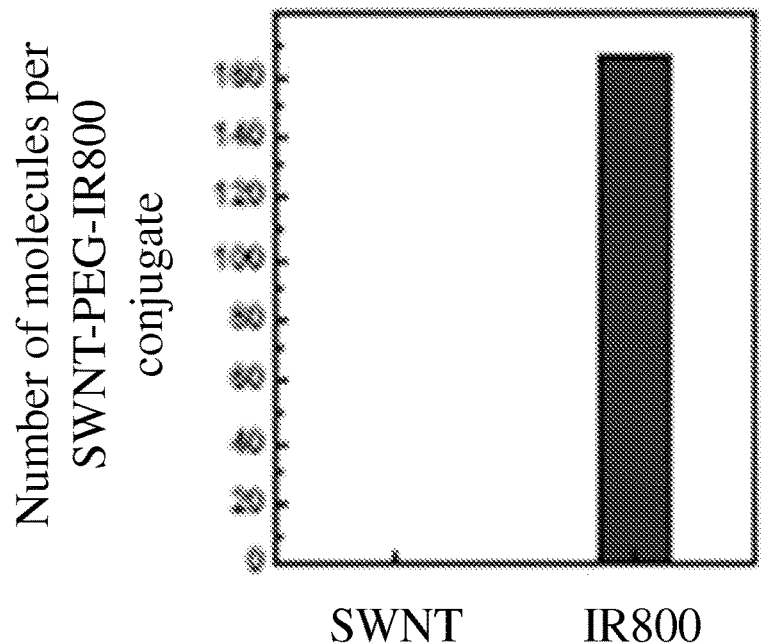
FIG. 5C is a graph showing calculated number of SWNT and IRDye-800 molecules in each SWNT-PEG-IRDye-800 conjugate, indicating on average 167 IRDye-800 molecules on each SWNT backbone. The large number of IRDye-800 molecules attached to SWNTs ensured sufficient NIR-I emitters despite fluorescent quenching of IRDye-800 of ~60% in 5A.

FIG. 5A shows the IRDye 800 fluorescence in free state compared to SWNT-PEG-IRDye 800, showing that substantial, but not all fluorescence was retained after conjugation to the SWNT. FIG. 5B shows data used to calculate the average number of SWNT and IRDye molecules in a conjugate.

UV-Vis-NIR Absorption Measurements

UV-Vis-NIR absorption spectrum of the as-made SWNT-IRDye-800 bioconjugate was measured by a Cary 6000i UV-Vis-NIR spectrophotometer, background-corrected for contribution from water. The measured range was 500-820 nm.

NIR Fluorescence Spectroscopy of SWNT-IRDye-800 Bioconjugate

NIR fluorescence spectrum was taken using a home-built NIR spectroscopy setup. The excitation source was a 200 W ozone-free mercury/xenon lamp (Oriel), which was dispersed by a monochromator (Oriel) to generate an excitation line with a central wavelength of 785 nm and a bandwidth of 15 nm. The excitation light was allowed to pass through the solution sample in a 1 mm path cuvette (Starna Cells, Inc.) and the emission was collected in a transmission geometry. The excitation light was rejected using a 790-nm long-pass filter (Semrock) so that the fluorescence of both IRDye-800 and SWNTs could be collected in the 790-1500 nm emission range. The emitted light was directed into a spectrometer (Acton SP2300i) equipped with a liquid-nitrogen-cooled InGaAs linear array detector (Princeton OMA-V). Spectra were corrected post-collection to account for the sensitivity of the detector and extinction feature of the filter using the MATLAB software.

Determination of Cytotoxicity of SWNTs

We determined the SWNT toxicity in vitro by MTS assay using a CellTiter96 kit (Promega) on human dermal microvascular endothelial cells (Lonza). ~5000 cells were incubated per well with 100 µl of EGM2MV growth media (Lonza) and serially diluted SWNT solution (n=3 for each concentration). The cells were kept at 37° C. in a humidified atmosphere containing 5% CO2 for 24 hours in the presence of SWNTs at different concentrations. Immediately before addition of 15 µL of CellTiter96, a colorimetric indicator of cell viability, the SWNT spiked medium was removed from each well plate and replaced with fresh medium. This prevented any interference in the absorbance readings from SWNTs. After 1 hour, the color change was quantified using a plate reader and taking absorbance readings at 490 nm. Cell viability was plotted as a fraction of the absorbance of control wells incubated without SWNTs.

Mouse Handling, Surgery and Injection 6-week-old female athymic nude mice were obtained from Charles River. All animal studies were approved by Stanford University's Administrative Panel on Laboratory Animal Care. Induction of unilateral hindlimb ischemia was performed according to our previous studies. Control, unsurgerized mice (n=4) and mice with induced ischemia (n=3) were used in the study. For the injection of nanotube solution, a 28 gauge syringe needle was inserted into the lateral tail vein, allowing for bolus injection with the room lights turned off during the first frames of imaging. All mice were initially anesthesized before imaging in a knockdown box with 2 L·min$^{-1}$ O$_2$ gas flow mixed with 3% Isoflurane. A nose cone delivered 1.5 L·min$^{-1}$ O$_2$ gas and 3% Isoflurane throughout imaging.

In vivo NIR Fluorescence Imaging with Tunable Magnifications

Figure 1B:
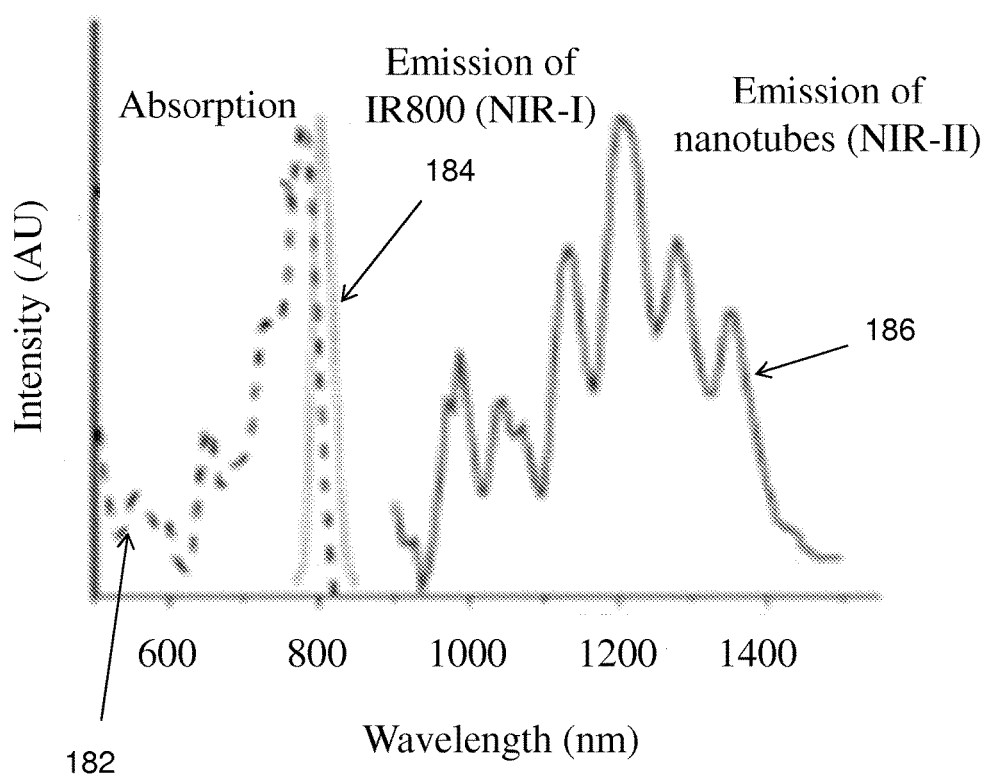
FIG. 1B is a graph showing the absorption spectrum of the SWNT-IRDye-800 conjugate (dashed curve 182), emission spectrum of IRDye-800 dye (sharp curve 184) and SWNTs (rightmost curve 186).
Figure 1C:
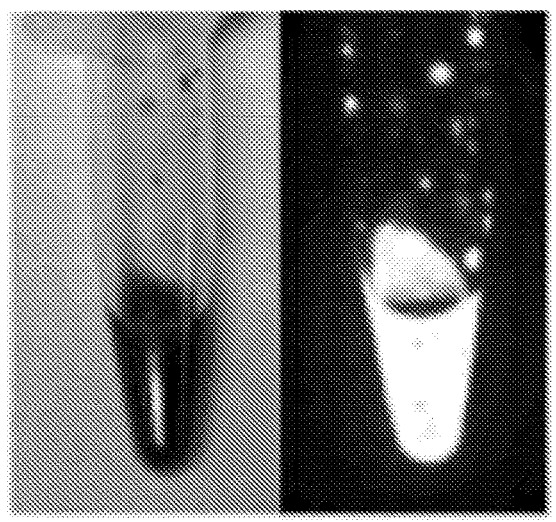
FIG. 1C is a digital photograph (left) and an NIR-II fluorescence image (right) of /injected solution containing 0.10 mg·ml-1 SWNT-IRDye-800 conjugates.
Figure 1D:
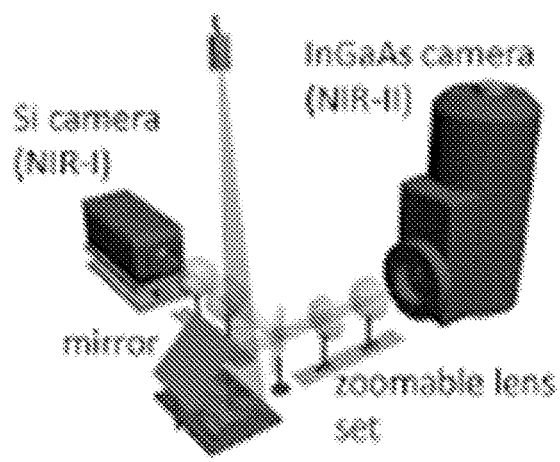
FIG. 1D is a schematic of the imaging setup showing simultaneous detection of both NIR-I and NIR-II photons using Si and InGaAs cameras. A zoomable lens set was used for adjustable magnifications.

Animals were mounted on a heated stage in the supine position beneath the laser at 10 min post injection. NIR fluorescence images were collected using a 1344×1024 pixel silicon CCD camera (Hamamatsu) for collecting photons in NIR-I and a liquid-nitrogen-cooled, 320×256 pixel two-dimensional InGaAs array (Princeton Instruments) for collecting photons in NIR-II. A flip mirror was used to switch photon collection between the two cameras (FIG. 1D). The excitation light was provided by a 785-nm diode laser (Renishaw) coupled to a 4.5-mm focal length collimator (Thorlabs) and filtered by a 790-nm bandpass filter with a bandwidth of 10 nm (Thorlabs). The excitation power density at the imaging plane was 8 mW·cm-2, much lower than the safe exposure limit of 296 mW·cm-2 at 785 nm determined by the International Commission on Non-ionizing Radiation Protection.40 The emitted light from the animal was filtered through a 790-nm long-pass filter (Semrock) and an 850-nm short-pass filter (Thorlabs) coupled with the Si camera for the NIR-I imaging window, or through a 900-nm long-pass filter (Thorlabs) and an 1100-nm long-pass filter (Thorlabs) coupled with the InGaAs camera for NIR-II imaging. A lens set was used for obtaining tunable magnifications, ranging from 1× to 2.5×magnification by changing the relative position of two NIR achromats (200 mm and 75 mm, Thorlabs), and from 2.5× to 7× magnification by changing the relative position of two other NIR achromats (150 mm and 200 mm, Thorlabs). A binning of 4 and an exposure time of 300 ms were used for the Si camera (1344×1024 pixels) to capture images in the NIR-I window, and a binning of 1 and an exposure time of 300 ms were used for the InGaAs camera (320×256 pixel) to capture images in the NIR-II window. Different binnings were used to compensate the difference of array size of the two cameras.

Microscopic Computed Tomography for Vascular Imaging

Micro-CT scans were performed using a MicroCAT II micro-CT scanner (Siemens Preclinical Solutions) using the following parameters: X-ray voltage 80 kVp, anode current 50 mA, and exposure time 2000 ms per 576 frames through 360° rotation. Mice were injected with blood pool contrast agent Fenestra VC (50 mg·ml-1 iodine, Advanced Research Technologies) intravenously into the lateral tail vein at 0.3 ml·(20 g)$^{-1}$ body weight with a 28-gauge needle. Animals (n=2) were scanned 1 h post-injection for 1 h total scan time. Three-dimensional reconstruction was performed by COBRA 1.5 and visualized using Amira 5.4. Resulting voxel dimension was 40 m.

Video-Rate Imaging in the NIR-II Window

Video-rate imaging was performed on the same homebuilt imaging system as in the steady-state imaging case except that only an InGaAs camera was used for imaging in the NIR-II window. The excitation light was provided by an 808-nm diode laser (RMPC lasers) coupled to a 4.5-mm focal length collimator (Thorlabs) and filtered by an 850-nm short-pass filter and a 1000-nm short-pass filter (Thorlabs). The excitation power density at the imaging plane was 140 mW·cm$^{-2}$, lower than the safe exposure limit 329 mW·cm$^{-2}$ at 808 nm.40 The emitted light from the animal was filtered through a 900-nm long-pass filter and an 1100-nm long-pass filter (Thorlabs) so that the intensity of each pixel in the InGaAs 2D array represented light in the 1.1 ~1.7 m range. A lens pair consisting of two achromats (200 mm and 75 mm, Thorlabs) was used focus the image onto the detector with a magnification of 2.5×. The InGaAs camera was set to expose continuously, and NIR-II fluorescence images were acquired with LabVIEW software. The exposure time for all images shown in the videos was 100 ms. There was an 87.5-ms overhead in the readout, leading to an average time of 187.5 ms between consecutive frames and a frame rate of 5.3 frames·s-1.

Dynamic Contrast-Enhanced Imaging Based on PCA

Dynamic contrast-enhanced images were obtained in a similar fashion to previous work by the Hillman group and our group. First 200 consecutive frames immediately after injection were loaded into an array using MATLAB software, and the built-in princomp function was used to perform PCA. Features with faster hemodynamic show up early in the video and are thus grouped in the negative fourth principal component. Features with slower hemodynamics show up later in the video and are thus grouped in the negative second principal component. Therefore negative pixels for the second principal component were color-coded in blue to represent venous vessels while negative pixels for the fourth principal component were color-coded in red to represent arterial vessels.

For tumor imaging and identification based on PCA, first 100 consecutive frames immediately after injection were loaded into an array using MATLAB software, and the built-in princomp function was used to perform PCA. The second, third and fourth principle components were arbitrarily assigned red, green and blue colors in the overlaid image. For vessel imaging and vessel type specification, empirically negative pixels for the second principal component were color-coded in blue to represent venous vessels while negative pixels for the fourth principal component were color-coded in red to represent arterial vessels in the overlaid image.

Quantification of Blood Velocity and Flow Based on NIR-II Fluorescence

Average region of interest (ROI) NIR-II fluorescence intensity was computed using MATLAB software within a given arterial region of each frame, which was determined by PCA analysis as explained in previous sections. Then the NIR-II fluorescence intensity was plotted as a function of time to reveal the change over 4 min after intravenous injection. The intensity in the femoral artery increased rapidly within the first 5-10 s before residing. The NIR-II intensity values were normalized against the maximum intensity within the ROI time traces to compensate for any differences in actual injection dose and relative fluorescence quantum yield. Linear fit was then performed on the rising edge of the normalized plot, and its slope (in %·s$^{-1}$) was translated into blood velocity in terms of cm·s$^{-1}$ by using the intensity-to-velocity conversion coefficient. Since the NIR-II signal increase was averaged over the ROI, the velocity value was the mean blood flow velocity along the femoral artery. Blood flow (F) in ml·min$^{-1}$ (cm$^3$·min$^{-1}$) was calculated based on the blood velocity (V) in cm·s$^{-1}$ and the diameter of the vessel (d) in m as follows: $F=\pi*(d/2)^2*V*6*10^{-7}$.

Validation of Intensity-to-Velocity Coefficient Based on Tubing Flow Model

A solution of SWNTs with known concentration was pumped by a syringe pump into catheter tubing with known diameter filled with purified water at a preset velocity (data not shown). The following settings were used for the standard condition: SWNT concentration=0.10 mg·ml$^{-1}$, SWNT fluorescence quantum yield (QY) ~2.5%, tubing diameter=760 m, tubing length within ROI (i.e., ROI length)=2.5 cm, fluid velocity=1.4 cm·s$^{-1}$ and tubing length before ROI (i.e., pre-ROI length)=8.5 cm. To screen the dependency of the coefficient on all these variables, the parameters were changed one at a time while keeping all others unchanged: SWNT concentration changed to 0.025 mg·ml$^{-1}$, SWNT fluorescence QY changed to 5.0%, tubing diameter changed to 380 m, ROI length changed to 1.25 cm, fluid velocity changed to 0.14 cm·s$^{-1}$ and pre-ROI length changed to 19.5 cm. Under each combination of settings, the NIR-II fluorescence intensity within the selected ROI was plotted as a function of time from immediately after injection to the time when intensity plateaued. Then NIR-II intensity values were normalized against the maximum intensity (plateau intensity) within the ROI time traces. Linear fit was then performed on the linear rise of each normalized plot to obtain a slope in %·s$^{-1}$. The intensity increase rate (slope) in %·s$^{-1}$ was then used to divide the velocity in cm·s$^{-1}$ to obtain the intensity-to-velocity conversion coefficient in cm·%$^{-1}$. For numerical simulation, a tubing linear flow model with axial mixing was adapted from a previous publication. A sigmoidal function with time and velocity dependence was used to simulate NIR-II intensity distribution at the flow front upon mixing using MATLAB software. The flow front function F(x,v,t) was given analytically by:

$$F(x, v, t) = \frac{I \cdot \varepsilon cd \cdot QY}{1 + e^{\frac{x - vt}{A_0 + Kvt}}}$$

where the excitation power density I, absorption coefficient , initial degree of mixing A0(~0.001cm) and mixing constant K (~0.5) are fixed, while concentration c, tubing diameter d, fluorescence quantum yield QY and velocity v were varied in the simulations to find the dependency of the coefficient. And the normalized ROI intensity was computed numerically as follows, $$I_{norm}(t) = \frac{\int_{x=L_{pre-ROI}}^{x=L_{pre-ROI}+L_{ROI}} F(x, v, t) \, dx}{\int_{x=L_{pre-ROI}}^{x=L_{pre-ROI}+L_{ROI}} F(x, v, +\infty) \, dx}$$

which was then plotted against time (date not shown). The linear rise region was fit to a linear equation, and the slope was used to divide the velocity, giving the intensity-to-velocity conversion coefficient:

$$Coeff. = \frac{v}{\frac{\partial I_{norm}(t)}{\partial t}}$$

Ultrasound for Quantifying Blood Flow in Femoral Artery

Ultrasound measurements were performed using a linear real-time transducer (40 MHz) connected to a Vevo 2100 ultrasound system (VisualSonics). The femoral artery was identified employing Duplex-ultrasonography (B-Mode and power Doppler). Flow velocity profiles were recorded by pw-Doppler imaging. Velocity-time integrals (VTI) and cardiac cycle length (CL) were measured using the Vevo 2100 device software. Arterial diameter (d) was known for each animal from previous NIR-II imaging. Femoral flow (F) was calculated as: F=Stroke volume (SV)*heart rate (HF)=arterial cross-sectional area (CSA)*VTI*HF =π*(d/2)$^2$*VTI*60,000/CL and averaged from three cardiac cycles.

Synthesis of Ag$_s$S Quantum Dots

The Ag$_2$S QDs were synthesized in organic phase according to a previously published method (Du et al., "Near-Infrared Photoluminescent Ag2S Quantum Dots from a Single Source Precursor," J. Am. Chem. Soc. 2010, 132, 1470-1471, which sets for a detailed description of the synthesis). Monodisperse Ag$_2$S quantum dots (QDs) were synthesized via pyrolysis of Ag(DDTC) in oleic acid, octadecylamine, and 1-octadecene. The uniform alkyl-capped Ag$_2$S QDs with a size of 10.2 nm emit near-IR emission at 1058 nm under 785 nm excitation.

Figure 8:
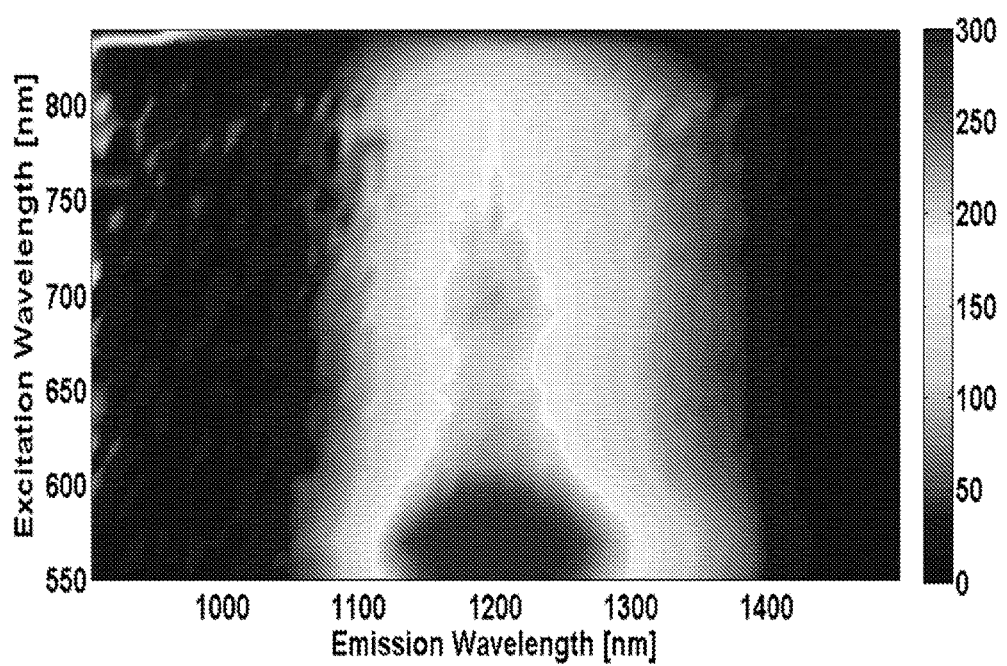
FIG. 8 is a photograph showing a photoluminescence versus excitation (PLE) spectrum of the 6PEG-$Ag_2S$ QD solution. Note the strong emission at 1200 nm that can be broadly excited from 550-820 nm.
Figures 9, 10:
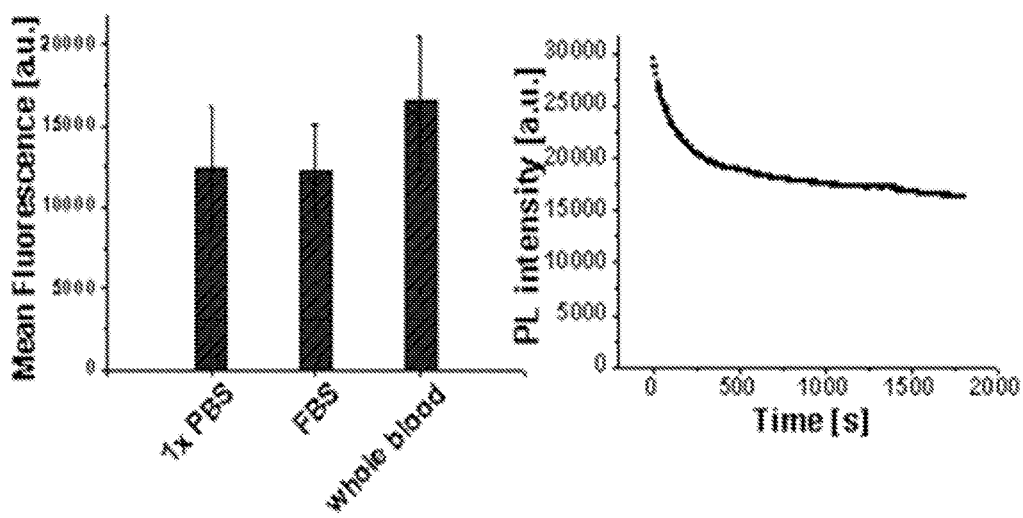
FIG. 9 is a graph showing the fluorescence stability of 6PEG-$Ag_2S$ QDs. The quantum dots at a concentration of 0.134 mg/mL are stable in 1x PBS (left), FBS (middle), and mouse whole blood (right) with no statistically significant change in NIR-II photoluminescence signal 24 h after mixing at room temperature.
FIG. 10 is a graph showing that after 30 minutes of irradiation with an 808 nm laser diode at 0.14 W/cm2, the 6PEG-$Ag_2S$ QDs retain over 50% of their initial NIR-II photoluminescence without significant further decay.

The hydrophobic Ag$_2$S QDs were then exchanged to a surfactant coating of dihydrolipoic acid (DHLA), and reacted with amine-functionalized six-armed PEG via ethyl (dimethylaminopropyl)-carbodiimide/N-hydroxysuccinimide (EDC/NHS) to afford highly water, buffer, and serum soluble 6PEG-Ag$_2$S QDs with average diameter of ~5.4 nm. The 6PEG-Ag$_2$S QDs were soluble and physically stable over >10 months in phosphate buffer saline (PBS) while retaining high fluorescence in the 1.0-1.4 μm NIR-II region upon excitation at 808 nm. A UV-Vis-NIR absorption spectrum of the 6PEG-Ag$_2$S QD solution showed increasing absorption in the shorter wavelengths, which was consistent with previous publications. [Du et al., above] The photoluminescence versus excitation (PLE) spectrum of the 6PEG-Ag$_2$S QD solution revealed the emission of Ag$_2$S QDs centered at 1200 nm (FIG. 8) and independent of excitation. The fluorescence quantum yield of 6PEG-Ag$_2$S QDs was determined as ~15.5%. The photostability of 6PEG-Ag$_2$S QDs was tested by continuous illumination of the 6PEG-Ag$_2$S QD solution with an 808 nm laser diode at 0.14 W/cm$^2$. The NIR-II photoluminescence (PL) intensity did decrease in the first ~200 s, but then stabilized and remained over 50% of its initial PL intensity over 0.5 h of continuous irradiation. Since the QDs were typically illuminated for less than 2 min during in vivo imaging, the 6PEG-Ag$_2$S QDs remained highly fluorescent in NIR-II without significant photobleaching through the imaging time.

In general, 0.1 mmol of $(C_2H_5)_2NCS_2Ag$ was added into 10 g of 1-dodecanethiol (DT) in a three-necked flask (100 mL) at room temperature. The slurry was vacuumed for 5 min to remove any residual oxygen under vigorous magnetic stirring, before being heated up to 210° C. at a heating rate of 15 ° C./min and staying at 210 ° C. for 1 h under $N_2$ atmosphere. Then the mixture was allowed to cool down to room temperature naturally. Subsequently 50 mL of ethanol was poured into the solution, and the resultant mixture was centrifugally separated with a centrifugal force of 6729 g for 20 min to collect the product. The as-made hydrophobic Ag$_2$S QDs with an average diameter of 5.4 nm coated with DT as the surface-capping ligand were obtained. To make Ag$_2$S QDs hydrophilic, ligand exchange was carried out to replace DT with DHLA. A mixture of as-prepared hydrophobic Ag$_2$S sample (0.05 mmol), cyclohexane (15 mL), ethanol (15 mL) and DHLA (0.15 g) were stirred at room temperature for 48 h. The product was then isolated by centrifugation with a centrifugal force of 26916 g for 20 min, washed with deionized water, and re-dispersed in deionized water. Then 24 mg of six-armed PEG (10 kDa) and 120 μL of EDC/NHS (20 mg/mL) were added into the DHLA-Ag$_2$S solution, sonicated for 30 min. Another 360 μL of EDC/NHS (20 mg/mL) were added, and stirred for 8 h. The product was then isolated by centrifugation with a centrifugal force of 26916 g for 20 min and washed with 1×PBS buffer, and re-dispersed in 1×PBS buffer.

6PEG-Ag$_2$S QDs samples were prepared by drying a drop of 6PEG-Ag$_2$S QDs solution on an amorphous carbon-coated copper grid. The morphology and size measurement were performed with a Tecnai G2 F20 S-Twin TEM (FEI, USA) operated at 200 kV. More than 100 particles were analyzed to get the average size of the 6PEG-Ag$_2$S QDs.

EXAMPLES

Example 1

NIR-I and NIR-II Fluorescence Imaging of Vasculatures

First, to glean the differences of in vivo NIR-I and NIR-II fluorescence imaging, we made biocompatible SWNT-IRDye-800 conjugates as dual-color imaging agents, where IRDye-800 (IRDye 800CW, LI-COR) was a commercial NIR-I fluorophore. High-pressure carbon monoxide conversion (HiPCO) SWNTs were stably suspended by biocompatible surfactants of 75% DSPE-mPEG (5kDa) and 25% DSPE-PEG(5kDa)-NH2 with amine groups covalently functionalized with IRDye-800 (FIGS. 1A and 5A-C). Both the SWNT and IRDye-800 label could be excited by a 785 nm laser, but exhibited different emissions. The IRDye-800 dye emitted at ~800 nm in the NIR-I, while the SWNT emitted in the 1.1-1.4 m NIR-II region (FIG. 1B). The dual-color emission of SWNT-IRDye-800 conjugate ensured co-localization of SWNTs and IRDye-800 dyes, and enabled us to image the same tissue in two distinct spectral windows so as to evaluate the performance of photons in different wavelengths for live animal imaging.

Figure 5D:
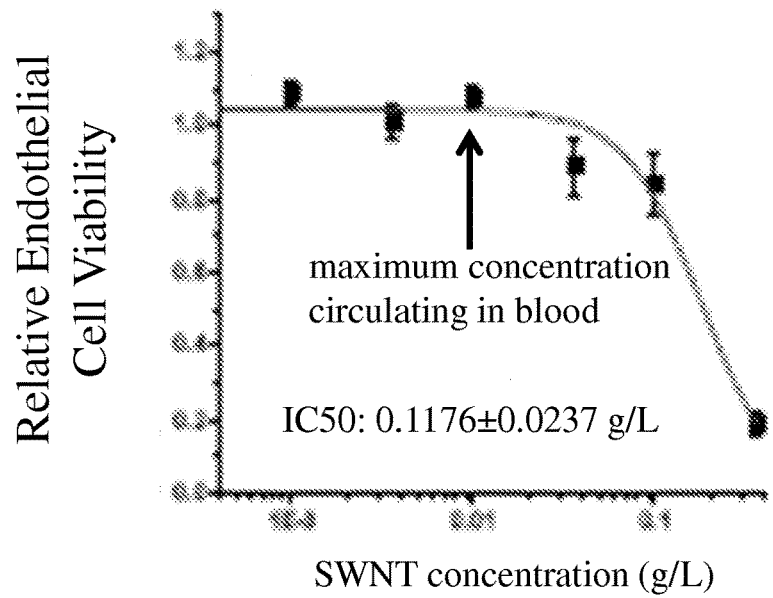
FIG. 5D is a graph showing a determination of half maximal inhibitory concentration (IC50) of SWNTs for endothelial cells. Original data (black squares) were fitted to sigmoidal function, revealing an IC50 value of 0.1778±0.0237 g/L. Error bars reflect the standard deviation of relative endothelial cell viability values from 3 wells of cells incubated at the same SWNT concentration.
Figure 6:
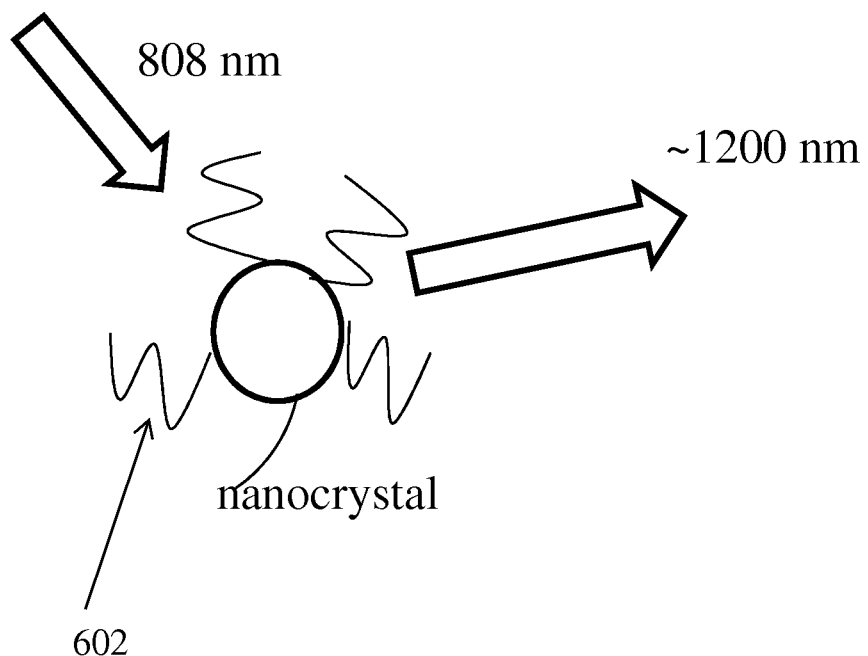
FIG. 6 is a schematic drawing of a quantum dot ("nanocrystal") embodiment of the present invention, with solubilizing hydrophilic polymer (PEG) shown at 602. 6PEG $Ag_2S$ QDs emit at 1200 nm upon excitation in the blood stream at 808 nm.

For parenteral administration and live animal imaging, we prepared and injected a solution (200 L) of 0.10 mg·mL-1 (1.0 mg·kg-1 body weight) SWNT-IRDye-800 conjugates (FIG. 1C) into a nude mouse intravenously. We estimated the maximum SWNT concentration in the blood would be 17×lower than the half maximal inhibitory concentration (IC50) of vascular endothelial cells (FIG. 5D). The circulation half-time of DSPE-mPEG functionalized SWNTs was ~5 h,8 and our previous studies had shown the lack of acute or long-term toxicity of such PEGylated SWNTs in vivo. The mouse was illuminated using a 785 nm laser at 8 mW·cm-2 (FIG. 1D) and imaged in the NIR-I (FIG. 1E-G) using a Si camera and in the NIR-II (FIG. 1H-J) using an InGaAs camera equipped with different emission filters. An adjustable lens set was used to obtain three different magnifications: lx (whole body), 2.5×(entire hindlimb) and 7× (partial hindlimb).

We found that all images in the NIR-I region employing IRDye-800 fluorescence manifested indistinct vascular anatomy. The corresponding cross-sectional intensity profiles were characterized by broad peaks (FIG. 1E-G, bottom). Presumably, these characteristics were related to significant scattering and absorbance of NIR-I photons, which limited the depth and resolution of traditional NIR imaging in vivo. In contrast, when the same mouse was imaged in the NIR-II region by detecting SWNT fluorescence, there was a substantially improved spatial resolution of vessels at all magnifications. Moreover, the NIR-II window clearly visualized smaller, higher-order branches of blood vessels at higher magnifications.

Cross-sectional intensity profiles all exhibited sharp peaks, with the calculated vessel diameter values consistent with expected values (FIG. 1H-J, bottom). In contrast, it was impossible to calculate vessel diameters based on the NIR-I images, in which we observed a 2-3-fold broadening of the cross-sectional profiles on average.

Example 2

NIR-II and micro-CT for Vessel Imaging

Figure 2A:
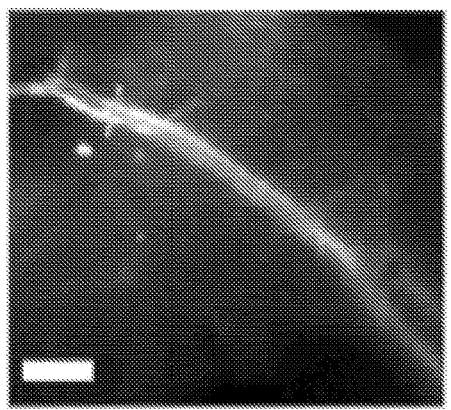
FIGS. 2A, 2B, 2C and 2D is a series of images showing NIR-II fluorescence and micro-CT imaging of hindlimb blood vessels.
Figure 2B:
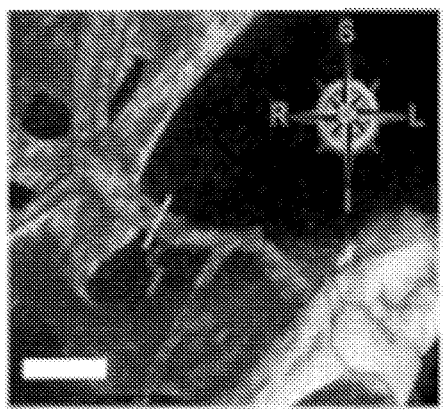
Figure 2C:
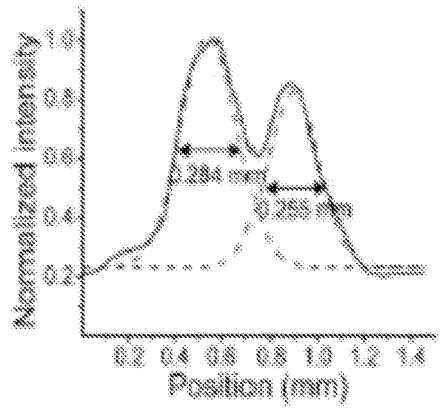
Figure 2D:
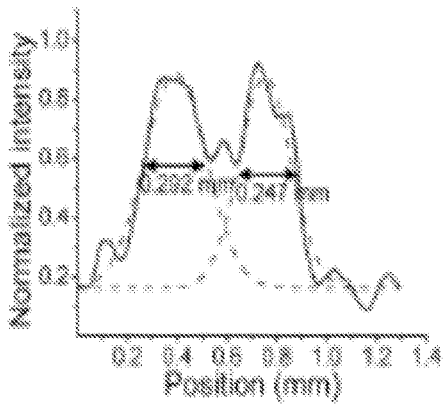

Micro-CT is a commonly-used three-dimensional (3D) X-ray imaging technique based on tomographic reconstruction with spatial resolution down to ~100 m and excellent penetration depth. Accordingly, we compared the spatial resolution of the proximal femoral artery and vein in the same mouse, achieved by NIR-II and micro-CT methods (FIG. 2A,B). A cross-sectional analysis was performed across the blood vessels in each image, and the corresponding intensity profiles are shown for NIR-II image (FIG. 2C) and micro-CT image (FIG. 2D). Two peaks were identified in each plot, corresponding to femoral artery and vein, and were fitted into two Gaussian functions to extract the widths. The vessel widths extracted from NIR-II image (0.284 mm and 0.255 mm) agreed with those from micro-CT image (0.292 mm and 0.247 mm). The analysis of micro-CT images validated the vessel diameters measured by NIR-II imaging, suggesting the two techniques are comparable in imaging vascular structures ~100s m in diameter.

To compare the resolution limits between NIR-II and micro-CT, we determined the smallest vessels these two techniques were able to discern. In the distal hindlimb of the mouse, the NIR-II image showed greater numbers of small vessels compared to the micro-CT image at the same location (FIG. 2E,F). The smallest measurable vessel by NIR-II had a Gaussian-fit diameter of only 35.4 m (FIG. 2G), while micro-CT could not discern any vessel smaller than ~100 m in diameter (FIG. 2H). Furthermore, NIR-II method generated images much faster than micro-CT (300 ms for NIR-II and 2 h for micro-CT).

Example 3

Differentiation of Arterial and Venous Vessels

To determine whether NIR-II fluorescence imaging could distinguish arterial from venous circulation, we monitored the blood flow inside the vessels by recording videos in the NIR-II window immediately upon tail-vein injection of SWNT fluorophores. To enable greater temporal resolution (i.e., shorter exposure time) for dynamic recordings, we used an 808 nm laser at 140 mW·cm-2 for more efficient excitation of SWNT fluorophores.

Figure 3E:
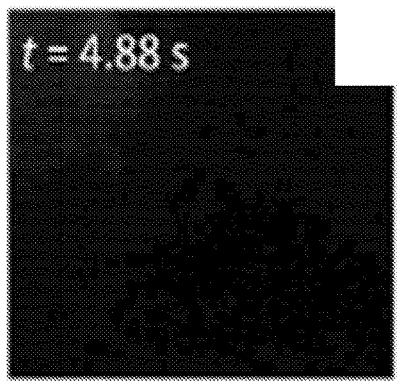
FIGS. 3E, 3F, and 3G is a series of three images showing a time course NIR-II fluorescence images of hindlimb blood flow in an ischemic animal.
Figure 3F:
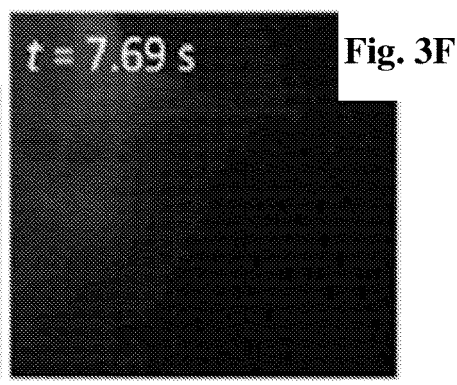
Figure 3G:
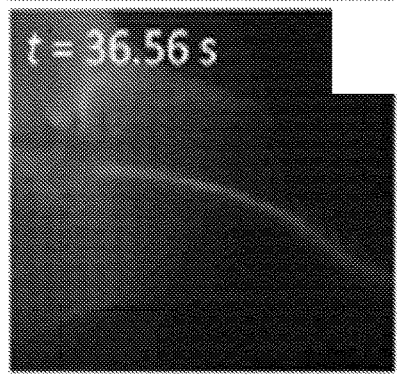
Figure 3H:
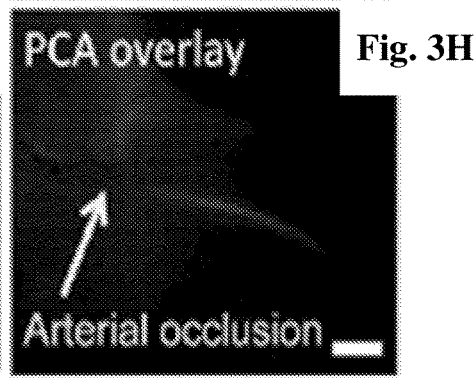
FIG. 3H is a PCA overlaid image based on the first 200 frames (37.5 s post injection) of the ischemic animal; only arterial vessels (shown by the arrow and, in the original image, color-coded in red) can be seen. The level of the experimentally induced arterial occlusion is indicated by the yellow arrow. All scale bars indicate 2 mm (white bar in 3H).

When a 200 L solution containing 0.10 mg·ml-1 biocompatible SWNTs was injected into the tail vein of a nude mouse (Mouse C1), we observed an NIR-II signal from the SWNTs in the proximal femoral artery within 5 s, and the entire femoral artery and some of the proximal musculature after ~8 s (FIG. 3A,B). Outflow of SWNTs into the femoral vein was reflected by the increased feature width (vascular bundle in the femoral sheath) at later time points but difficult to distinguish from the femoral artery by visual inspection due to their proximity (FIG. 3C). However, due to the time delay in the first appearance of the signal in the artery to its later appearance in the vein, it was possible to employ PCA to differentiate the two types of vessels. Essentially, the PCA approach assigns image pixels to groups (components) based on their variance, i.e., pixels that vary similarly in time. We applied PCA to the video-rate images and clearly discriminated the arterial component from the venous component. By convention we color-coded the arterial PCA component in red and the venous component in blue (FIG. 3D). Similar results were obtained with an additional three mice (data not shown).

We repeated these studies in mice after surgically inducing unilateral hindlimb ischemia (Mouse I 1-3). In this model, ligation and excision of the proximal superficial femoral artery and ligation of the deep femoral artery reduced limb perfusion by ~80% in the immediate postoperative period. On the first postoperative day, we studied mice with SWNT-assisted NIR-II fluorescence imaging. After tail vein injection of SWNTs, we observed a marked delay in the appearance of fluorescent signals in ischemic limbs (FIG. 3E-G) compared to healthy limbs. As in normal animals, we performed PCA on the first 200 frames (~37.5 s) of video-rate recording of the ischemic animal. However, due to the markedly reduced perfusion, venous return in the ischemic limb could not be observed at this time point (FIGS. 3). It was necessary to continue imaging for an extended period (>2 min) to visualize the femoral vein (data not shown). This delay in venous return was consistent with severe limb ischemia.

We also applied the dynamic contrast PCA approach to demonstrate that arteries and veins subserving a larger region of tissue could be distinguished. In these studies, we imaged a larger field of view including both the abdominal and femoral regions. Within 5 s of tail vein injection, signals were observed in the aorta as well as the iliac, femoral and epigastric arteries and their branches in the abdomen and pelvis (data not shown). The NIR-II signal from these vessels peaked and then subsided by ~10 s post injection with increasing intensity in the tissue (data not shown). Subsequently, signals were observed in veins draining these regions, including the previously identified femoral vein and hypogastric veins (data not shown). As before, we used PCA to assign pixels to arterial or venous conduits based on their time variance (data not shown), where arteries and veins were resolved. Notably, even the aorta can be seen in supine position of the mouse, indicating a penetration depth of >5 mm for NIR-II imaging. This result confirmed the capacity of NIR-II dynamic contrast-enhanced imaging to distinguish arteries from veins.

Example 4

Blood Flow Quantification in Ischemic and Control Limbs

Figure 4A:
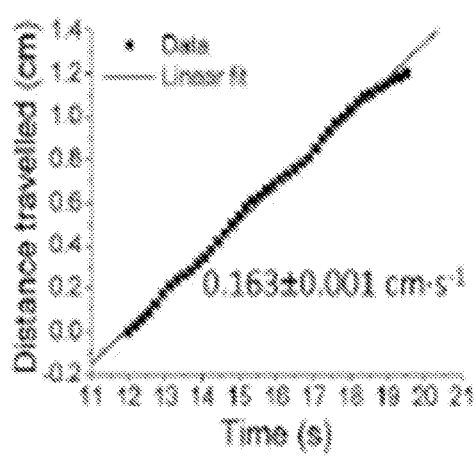
FIGS. 4A, 4B, and 4C is a series of graphs showing femoral artery blood velocity quantification for an ischemic hindlimb (slower flow) compared to a healthy, control hindlimb (FIG. 4D, E) by NIR-II imaging and ultrasound.

NIR-II imaging revealed a dramatic delay in the appearance of fluorescence signal in ischemic hindlimbs versus control healthy limbs. We then assessed blood flow in the ischemic hindlimb of Mouse I 1quantitatively. From 12 s to 19.5 s post injection of SWNTs, propagation of the signal could be visualized from the proximal site of arterial occlusion to the distal femoral artery (data not shown), presumably filling through collateral channels. The position of the signal front at each time point was then extracted from each frame and plotted against time, showing a linear relationship of flow distance vs. time with a blood velocity of 0.163 cm. s-1 (FIG. 4A). To calculate blood flow, we measured the mean diameter of the femoral artery (174 m). The measurement of blood flow velocity and arterial diameter permitted the calculation of femoral artery blood flow (2.33×10-3 mL·min-1).

Figure 4B:
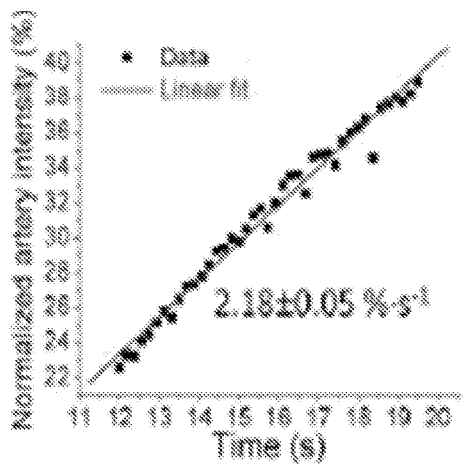
Figure 4C:
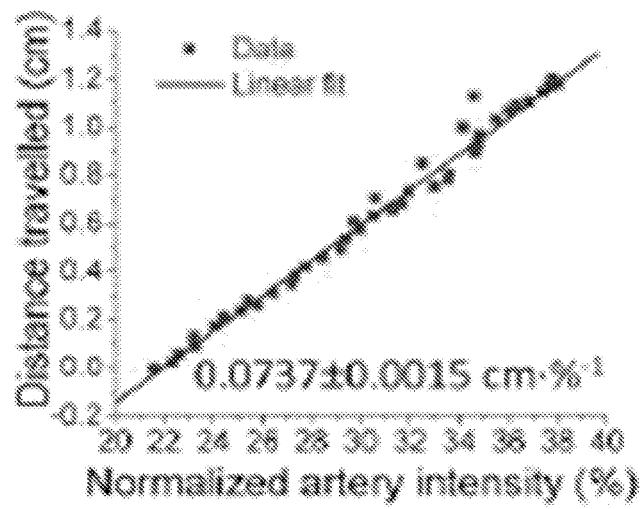

We found the progression of NIR-II signal through the femoral artery in normal mice was so rapid that our current video imaging rate lacked sufficient temporal resolution. Alternatively, to assess blood velocity in these animals, we measured the increase in signal intensity in a region of interest (ROI) (a pre-defined segment of the femoral artery from PCA). We normalized the signal intensity to compensate for differences in actual injected dose or fluorescence quantum yield, and plotted the average ROI intensity vs. time (see Methods). In the animal with hindlimb ischemia, we observed an NIR-II intensity increase of 2.18%·s-1 (FIG. 4B). Blood flow and NIR-II intensity were then plotted against each other (FIG. 4C) to yield a linear slope of ~0.0737 cm. %-1 that correlated velocity with intensity change. We used this coefficient to convert the NIR-II intensity increase rate to blood velocity, in the normal animals where blood velocity exceeded the temporal resolution of our current imaging device. To further establish this translation coefficient, we reproduced the blood velocity quantification with two other ischemic mice, 12 and 13, and obtained an average value of 0.0747±0.0019 cm·%-1 (Table 1).

TABLE 1

Establishing the intensity-to-velocity conversion coefficient for translating NIR-II signal increase to blood velocity

| Ischemic Mouse Number | Conversion Coefficient [cm-%$^{-1}$] |
|---|---|
| 1 | 0.0737 |
| 2 | 0.0773 |
| 3 | 0.0730 |
| Average | 0.0747 ± 0.0019 |

Figure 4D:
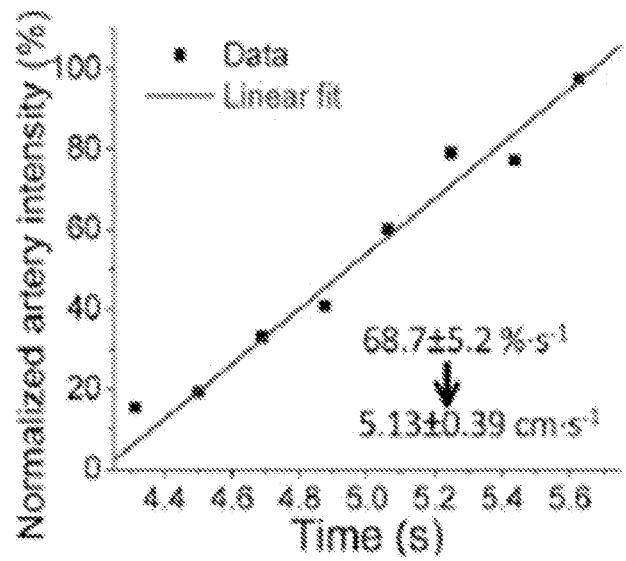
FIG. 4D is a graph showing normalized NIR-II signal in the femoral artery versus time.

The intensity-to-velocity conversion coefficient was applied to measurements of femoral artery blood flow in a healthy, control mouse, where the blood velocity was so rapid that our current NIR-II imaging device was unable to track a discrete flow front over time (data not shown). Alternatively we measured the NIR-II intensity change in an ROI of the femoral artery as a function of time (FIG. 4D), revealing a normalized NIR-II intensity increase of 68.7±5.2%·s-1 before it peaked. By using the conversion coefficient of 0.0747 cm·%-1, we were able to translate the intensity increase to a blood velocity of 5.13±0.39 cm. s-1. To validate this measure of blood velocity, we used ultrasonography to obtain a Doppler-derived velocity in the same mouse at the same ROI of the femoral artery, by an operator blinded to the SWNT imaging values. In the same animal, the ultrasound measurement provided a Doppler-derived velocity of 4.97±0.17 cm. s-1 (FIG. 4E), which was in good agreement with the NIR-II video-imaging result (a deviation of ~3%).

To further validate our intensity-to-velocity conversion coefficient and to understand the physics behind it, we used a simplified fluid dynamic system, in which SWNT solution was pumped into catheter tubing filled with purified water (data not shown), and derived the coefficient based on NIR-II intensity increase (see Methods). By changing the experimental settings one at a time, we found the coefficient remained invariant (0.0764±0.0025 cm. %-1) as we varied the injected SWNT concentration, SWNT fluorescence quantum yield, tubing diameter, ROI length and velocity. It did vary with the distance between the injection site and ROI (pre-ROI length) (Table 2).

TABLE 2

Dependency of the intensity-to-velocity conversion coefficient on six different variable based on experimental tubing flow results and numerical simulation

| Variable Control | Experimental Results [cm-% – 1] | Simulation Results [cm-% – 1] |
|---|---|---|
| Standard Settings | 0.0778 | 0.0730 |
| Change SWNT Concentration | 0.0739 | 0.0730 |
| Change SWNT Quantum Yield | 0.0756 | 0.0730 |
| Change Tubing Diameter | 0.0766 | 0.0730 |

TABLE 2-continued

Dependency of the intensity-to-velocity conversion coefficient on six different variable based on experimental tubing flow results and numerical simulation

| Variable Control | Experimental Results [cm-% − 1] | Simulation Results [cm-% − 1] |
|---|---|---|
| Change ROI Length | 0.0789 | 0.0780 |
| Change Fluid Velocity | 0.0757 | 0.0722 |
| Change Pre-ROI Length | 0.1648 | 0.1701 |

This finding was also confirmed by numerical simulations (Table 2) based on a linear flow model with axial mixing.[29] In the context of in vivo blood velocity quantification, since the pre-ROI length simply reflected the length of blood vessels in which the injected SWNTs had to travel before reaching the femoral artery, the coefficient should be invariant given the same type of animals with roughly same blood volume and therefore applicable from ischemic to control mice.

Figure 4E:
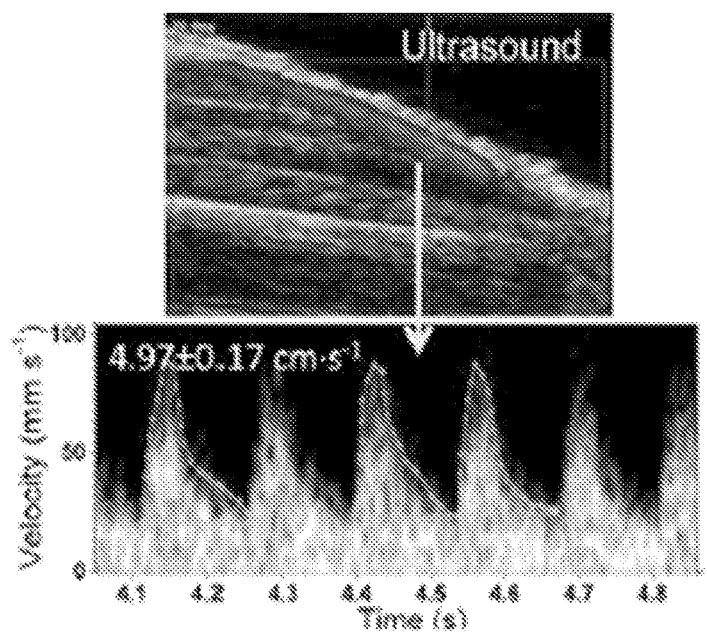
FIG. 4E is a photograph showing ultrasound measurement (top) of femoral artery blood velocity in the same mouse as in FIG. 4D based on integration of three outlined pulses (bottom).
Figure 4F:
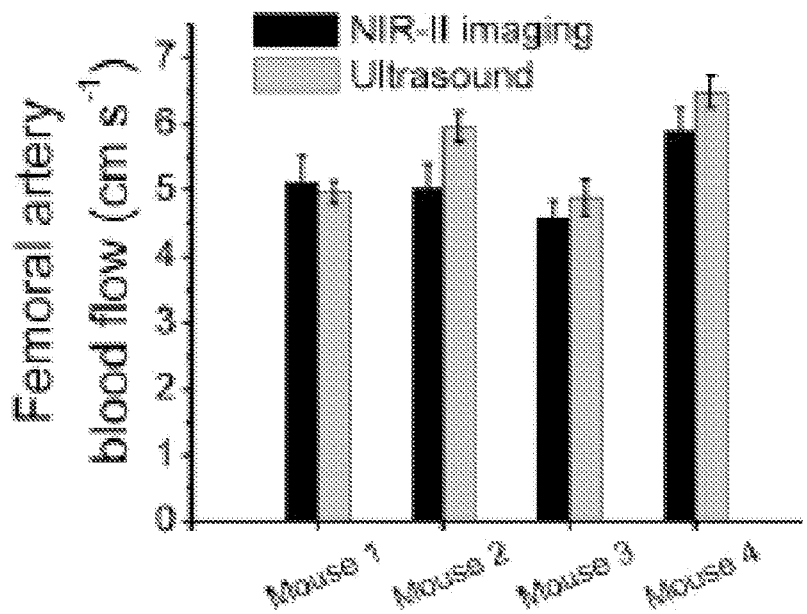
FIG. 4F is a bar graph showing a side-by-side comparison of femoral artery velocity obtained from NIR-II method (black) and ultrasonography (gray) for four control healthy mice. Black error bars were based on linear-fitting errors of NIR-II intensity increase plot, while gray error bars reflected the s.d. of three integrated pulses from ultrasonography.
Figure 4G:
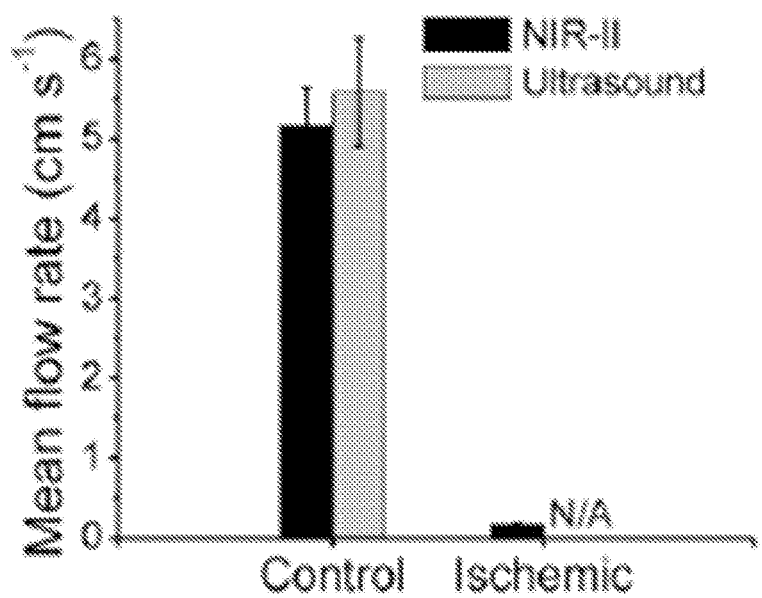
FIG. 4G is a bar graph showing the average femoral artery blood velocity of control group (n=4) and ischemic group (n=3), measured by NIR-II method (black) and ultrasound technique (gray). The ischemic blood velocity was not measurable by ultrasonography (shown as 'N/A'). Errors bars reflect the s.d. of each group.

To demonstrate the reproducibility of the NIR-II fluorescence-based blood velocity quantification, we compared the Doppler-derived velocities to those of the NIR-II method in three additional control animals (data not shown). A summarized plot suggested excellent agreement of results between the two methods (FIG. 4E). Subsequently, we performed these studies in three ischemic mice. The marked reduction in blood velocity in ischemic limbs (FIG. 4G) measured by NIR-II method was consistent with previous reports. It was noteworthy that blood velocity in the ischemic animals was low and beyond the detection capability of ultrasonography. Clearly, the NIR-II imaging technique proved advantageous over ultrasound by providing a broader dynamic range of blood velocity measurements in vivo.

Example 5

In vivo Imaging using PEG-Ag$_2$S quantum Dots, with PCA Analysis

6PEG-Ag$_2$S QDs prepared as described above were injected a 200 μL solution of 6PEG-Ag$_2$S QDs at a concentration of ~1.34 mg/mL (~13.4 mg/kg dose) intravenously into the tail vein of a female Balb/c mouse with a subcutaneous xenograft 4T1 murine tumor located on the right hindlimb. Immediately after injection, fluorescence images over the NIR-II region (1.1-1.7 μm) were collected continuously by a two-dimensional InGaAs array detector (Princeton) to track the blood circulation of Ag$_2$S QDs in real time under the excitation of an 808-nm laser at a power density of 0.14 W/cm$^2$, lower than the safe exposure limit of 0.33 W/cm$^2$ at 808 nm for small animals. A movie was made to show the video-rate NIR-II fluorescence images up to ~210 s post injection (p.i.) at a frame rate of 8.4 frames/sec. 6PEG-Ag$_2$S QDs entered the venous blood from the tail vein and first circulated through the heart and lungs to be oxygenated in the first ~3 s p.i. This corresponded to the pulmonary circulation of the cardiovascular system, followed by systemic circulation in other organs such as the kidneys. Besides the pulmonary and systemic circulations that could be clearly distinguished from the video-rate imaging, another interesting feature was the accumulation of NIR-II fluorescence signal in the tumor region, starting at ~15 s p.i. The NIR-II signal in the tumor region continued to increase from ~15 s p.i. to ~2 min p.i. The vascular structure of the tumor also became distinguishable over time. Thus, video-rate NIR-II fluorescence imaging based on 6PEG-Ag$_2$S QDs afforded immediate pinpointing of the location of the tumor within 2 min post injection.

To further distinguish the organs and the tumor based on dynamic contrast, principal component analysis (PCA) was applied to the first 100 frames (up to 11.9 s p.i.). PCA overlaid image after computation showed three distinct components (coded with orthogonal false-colors), corresponding to the lungs (blue) kidneys (red) and the tumor (green) [all colors in original only]. PCA grouped pixels into a component with similar time-dependent intensity change profiles, and therefore was able to discriminate various organs as QDs circulated through the organs. Owing to the dynamic contrast, PCA was more sensitive in pinpointing the tumor within a shorter time post injection than the video-rate imaging itself (~12 s p.i. for PCA vs. ~2min p.i. for real space video imaging.

We monitored the NIR-II signal, which reflected the distribution of 6PEG-Ag$_2$S QDs inside the mouse, over a longer period of time up to 24 h post tail-vein injection Due to the enhanced permeability and retention (EPR) effect of the tumor vasculature, steady increase of NIR-II fluorescence of 6PEG-Ag$_2$S QDs in the tumor region, as well as the decrease of NIR-II fluorescence in other organs and skin, was observed from 30 min p.i. to 24 h p.i., leading to increased tumor-to-background ratio (TBR) over time. The TBR was well above the Rose's number of 5 for 4-24 h p.i., indicating a positive imaging and detection of the tumor, according to the Rose criterion. Visual inspection of the same mouse also gleaned high uptake of Ag$_2$S QDs in the tumor area that darkened due to QD accumulation at 24 h p.i.

Example 6

Effectiveness of the Biocompatible Surface Coating of the Quantum Dots

To evaluate the effectiveness of biocompatible surface coating of Ag$_2$S QDs, blood circulation half-life of the 6PEG-Ag$_2$S QDs was determined to be 4.37±0.75 h based on a fit to first-order exponential decay of NIR-II fluorescence intensity of the blood samples (data not shown), suggesting high biocompatibility and slow uptake by the reticuloendothelial system (RES) compared to the half-life of linear PEG-coated QDs ($t_{1/2}$<12 min for CdSe/ZnS-PEG$_{750}$ and $t_{1/2}$~2 h for CdSe/ZnS-PEG$_{5000}$). To quantify the biodistribution of the 6PEG-Ag$_2$S QDs, mouse organs were collected 72 h after injection, when most of the injected QDs stopped circulating in blood. The QD biodistribution in the organs was found by two independent methods based on NIR-II fluorescence (data not shown) and inductively coupled plasma-mass spectrometry (ICP-MS) (data not shown).

The 6PEG-Ag$_2$S QDs ended up primarily in the RES organs including the liver and spleen, while the tumor uptake of the 6PEG-Ag$_2$S QDs measured by the ICP-MS method was ~10% ID/gram. The non-targeted (passive) tumor uptake of ~10% ID/gram was one of the highest tumor uptake values reported to date for intravenously injected QDs. The highest reported %ID/gram tumor uptake of quantum dots, based on fluorescence intensity, was approximately 20% ID/gram at 4 h p.i. and dropped to 7% by 24 h p.i. In contrast, the 6PEG-Ag$_2$S QDs maintain a 10% ID/gram tumor accumulation even at 72 h p.i. based on ICP-MS. The relatively long circulation time and high tumor uptake indicated that the 6PEG-Ag$_2$S QDs were well-passivated with branched PEG functionalization, which limited the opsonization of proteins for rapid RES uptake.

Example 7

In vivo Imaging of Sub-Millimeter Size Features using PEG-Ag$_2$S Quantum Dots

To exploit the high signal-to-background ratio in the NIR-II region we used the 6PEG-Ag$_2$S QDs prepared as described above for fast detection and imaging of tumors with sub-1 mm$^3$ size. Despite the ultra-small size of the tumor, 6PEG-Ag$_2$S QDs accumulated in the tumor through the EPR effect 24 h p.i. to light up the tumor over a completely dark background with a TBR of 16.7. We used a zoomed-in view of the tumor and found its size of ~1 mm×0.5 mm, with a volume of ~0.1 mm$^3$ according to the modified ellipsoidal formula (1 mm×0.5 mm×0.5 mm×½=0.125 mm$^3$). The high accumulation of QDs in the tumor was also suggested by the visibly darkened speck on the skin indicating the location of the tumor, which was otherwise unidentifiable due to its small size. After 5 days p.i. of 6PEG-Ag$_2$S QDs the tumor grew large enough to be seen visibly which also proved the previous tumor location contrasted by the QDs. The lower size limit of tumor imaging using Ag$_2$S QDs (~0.1 mm$^3$ in vivo) well exceeded previous reports of smallest detectable tumor size (~1 mm$^3$ ex vivo, van Dam et al., "Intraoperative tumor-specific fluorescence imaging in ovarian cancer by folate receptor-a targeting: first in-human results," Nature Medicine 17:1315-1319 (2011), owing to the high signal to background ratio in NIR-II and high tumor uptake of long circulating 6PEG-Ag$_2$S QDs.

For ultrasmall tumor imaging, three mice (n=3) were inoculated with ~1 million 4T1 murine breast cancer cells on the right hindlimb only. 200 µL solution of 6PEG-Ag$_2$S QDs at 1.34 mg/mL concentration was injected intravenously as the tumor contrast agent ~10 min after tumor inoculation. A small xenograft tumor (<1 mm$^3$) formed one day after inoculation, which was barely visible or palpable by the measuring tools. During injection, the mice were anesthesized using a 2 L/min oxygen flow with 3% Isoflurane. After imaging, mice were monitored until full consciousness and mobility was regained. In order to perform video-rate imaging and dynamic contrast-enhanced imaging based on PCA, the injection was done in the dark.

Example 8

In vivo Imaging using PEG-Ag$_2$Quantum Dots

Figure 11A:
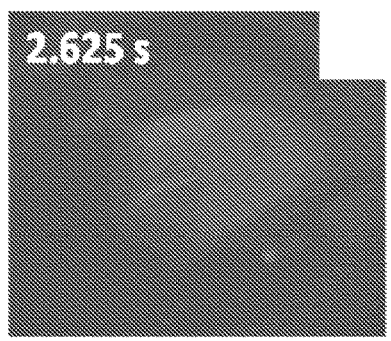
FIGS. 11A, 11B, 11C, and 11D is a series of four photographs showing blood vessel imaging and vessel type differentiation based on NIR-II fluorescence of 6PEG-$Ag_2S$ QDs. Photographs (11A-11C) are zoomed in time course NIR-II fluorescence images after 6PEG-$Ag_2S$ QD infusion showing blood flow in the left hindlimb of a mouse. The femoral arterial and venous vessels could be clearly seen within ~8 seconds after injection while smaller distal branched vessels began to appear as well. Photograph (11D) is a PCA overlaid image based on the first 40 frames (7.5 s post injection) showing the differentiation of arterial (red in original) and venous (blue in original) vessels. The scale bar indicates 5 mm for all images. Note the same left hindlimb of the same mouse in its supine position is shown in all images, where the main body of the mouse is to the left of each image while the left hindpaw is to the right of each image.
Figure 11B:
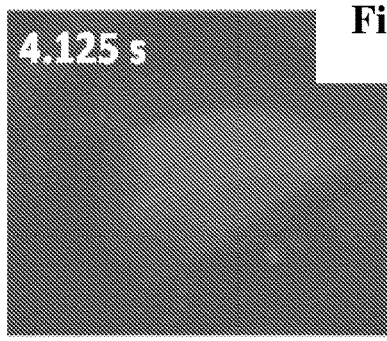
Figure 11C:
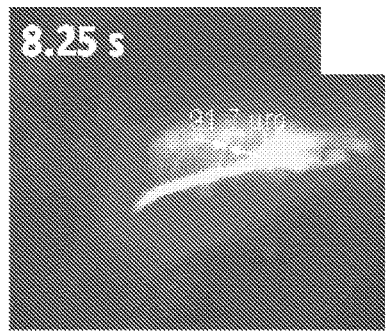
Figure 11D:
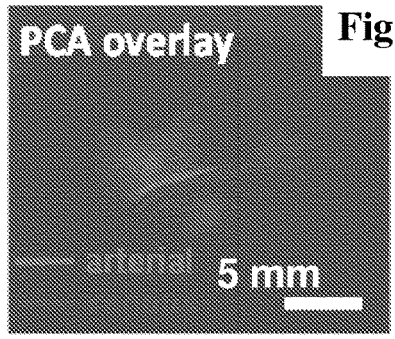

The bright NIR-II fluorescence and deep tissue penetration of NIR-II photons of Ag$_2$S QDs were used for fast imaging of vascular structures millimeters below the skin, a unique capability of NIR-II imaging. Upon injection of 200 µL of 6PEG-Ag$_2$S QD solution (1.34 mg/ml) into the tail vein of a Balb/c mouse), NIR-II emission signal in the femoral artery was observed ~3 s after injection (FIG. 11A), which continued to increase in intensity over time. The outflow of 6PEG-Ag$_2$S QDs in the femoral vein (immediately below the femoral artery) could be observed ~4 s after injection (FIG. 11B), and the NIR-II fluorescence intensity kept increasing in the region over time, adding to the overall width of the vessels and thus making the femoral vein difficult to distinguish from the femoral artery (FIG. 11C). We then made use of the time delay in the appearance of the NIR-II signal in the femoral veins vs. arteries to differentiate the two types of vessels into two components by PCA. Following medical convention, we assigned red color to the arterial component and blue color to the venous component, and overlaid these two components to form a vessel-type speed-differentiated image (FIG. 11D). Furthermore, some smaller vessels at the distal end of the hindlimb could be observed at ~8 s p.i. The smallest vessel that could be unambiguously identified by using QDs was found to have a diameter of ~90 µm (FIG. 11C).

For blood vessel imaging, animals were mounted on the imaging stage in the supine position beneath the laser. The same 2D InGaAs detector, 808-nm diode laser, filters and lenses were used as in tumor imaging, except that a magnification of 2.5× was used to zoom into the area of interest in the hindlimb. Since blood vessel imaging relied on the dynamic contrast generated by the blood flow in real time, the InGaAs camera was set to expose continuously for video-rate imaging, and NIR-II fluorescence images were acquired with LabVIEW software. The exposure time for all images shown in the videos was 100 ms, with an overhead time of 87.5 ms in the readout (different from video-rate tumor imaging), leading to an average time of 187.5 ms between consecutive frames and a frame rate of 5.3 frames per second.

Example 9

Toxicit Study of PEG-Ag2S

A complete in vivo toxicology study of 6PEG-Ag$_2$S QD showed minimal toxicity at a dose up to 30 mg/kg (i.e., >2-fold higher than used in this work) to the treated mice over a period of 2 months as evidenced by blood biochemistry, hematological analysis and histological examinations. Nevertheless, to gain a better understanding of the clearance pathway of this novel NIR-II fluorophore from the body, we studied the short-term retention and excretion after a single-dose injection of the 6PEG-Ag$_2$S QDs into tumor-free Balb/c mice (n=4). Feces and urine were collected on a daily basis for quantitative measurement of Ag$_2$S QDs based on ICP-MS. Excretion measurements revealed the excretion of 6PEG-Ag$_2$S QDs mainly through the biliary pathway at a steady rate, which was expected since the hydrodynamic radius of the 6PEG-Ag$_2$S QDs was ~26.8 nm according to dynamic light scattering (DLS), far larger than the renal filtration cut-off size of 5 nm. The biodistribution of the 6PEG-Ag$_2$S QDs was also examined at 24 h and 168 h (7 days) p.i. By 7 days p.i., the Ag$_2$S QDs were nearly cleared from all organs aside from the liver and the spleen.

For blood circulation analysis, at various time points p.i. of 6PEG-Ag$_2$S QDs, 5-10 µl of blood was taken from tail artery of 3 mice. Fluorescence imaging was used to compare the blood NIR-II fluorescence with a certain volume of control, QD-free blood spiked with a known concentration of the injected 6PEG-Ag$_2$S QD solution. After subtraction of the minimal blood autofluorescence, the % injected dose (ID) of QDs/gram of blood was determined. A first order exponential decay was fitted to the data, giving an accurate model of the Ag$_2$S QD blood clearance time.

For ex vivo biodistribution analysis, 72 h after injection of 6PEG-Ag$_2$S QDs, six injected mice were sacrificed, along with the non-injected mouse. Organs were collected and weighed; for three mice, the organs were dissolved by mixing with 1 ml of tissue lysis buffer (1% SDS, 1% Triton X-100, 40 mM tris acetate, 10 mM EDTA, 10 mM DTT) followed by using a hand-blender to grind the organs. Lastly, the organs were heated at 70 ° C. for 2 h to create a homogenous solution. The NIR-II fluorescent signal of each organ was then collected and normalized using the control mouse organ. The control mouse organs were dissolved in a similar fashion and initially imaged for autofluorescence, and then spiked with a known concentration of the injected 6PEG-$Ag_2S$ QD solution and imaged over time to see the initial fluorescence as well as if any drop in QD NIR-II fluorescence occurred in the dissolved organ. For all organs except the liver, the QD fluorescence did not drop over time. After the fluorescence signal was normalized for all organs, the % ID/gram was determined, giving a semi-quantitative measure of $Ag_2S$ QDs biodistribution. On the other hand, inductively-coupled plasmon-mass spectrometry (ICP-MS) was used to quantitatively confirm the fluorescence-based biodistribution. The organs from the other three mice were dissolved in 35% $HNO_3$ and heated at 70° C. for 12 h. The organs were then diluted 2000× in water and submitted for ICP-MS at the Environmental Measurement I: Gas-Solution Analytical Center at Stanford University. The %ID/gram values of $Ag_2S$ QDs in all analyzed organs were determined by comparing the Ag concentration to the injected solution as reported by ICP-MS, giving a quantitative measure of QD biodistribution.

The short term excretion of the 6PEG-$Ag_2S$ QDs suggests the biliary clearance as the main clearance pathway.

CONCLUSION

The above specific description is meant to exemplify and illustrate the invention and should not be seen as limiting the scope of the invention, which is defined by the literal and equivalent scope of the appended claims. Any patents or publications mentioned in this specification are indicative of levels of those skilled in the art to which the patent or publication pertains as of its date and are intended to convey details of the invention which may not be explicitly set out but which would be understood by workers in the field. Such patents or publications are hereby incorporated by reference to the same extent as if each was specifically and individually incorporated by reference, as needed for the purpose of describing and enabling the method or material to which is referred.

What is claimed is:

1. A method of determining flow velocity of a fluid in a lumen-forming structure, comprising the steps of:
   (a) delivering to said lumen-forming structure solubilized nanostructures that fluoresce in a near infrared II ("NIR-II") region of 1000 to 1700 nm, wherein the lumen-forming structure is a blood vessel, lymph duct, bile duct, or milk duct;
   (b) fluorescently exciting nanostructures from step (a) present within said lumen-forming structure;
   (c) collecting NIR-II fluorescence emitted from nanostructures excited in step (b); and
   (d) determining the flow velocity in a region of interest (ROI) in the lumen-forming structure by analyzing fluorescence emission collected in step (c) at a spatial resolution between 2-10 µm and a temporal resolution down to 10 msec per frame and measuring changes in average NIR-II fluorescence emission intensity over time in the ROI.

2. The method of claim 1, wherein the analyzing comprises principal component analysis ("PCA") of blood flow hemodynamics to assign colors to components of images and differentiate veins versus arteries.

3. The method of claim 1, wherein said delivering is by intravenous injection, subcutaneous injection, or intramuscular injection.

4. The method of claim 1, wherein the solubilized nanostructure is a carbon nanostructure.

5. The method of claim 4, wherein the carbon nanostructure is a single walled nanotube ("SWNT").

6. The method of claim 1, wherein the solubilized nanostructure is a carbon nanostructure solubilized with polyethylene glycol ("PEG").

7. The method of claim 1, wherein the solubilized nanostructure is a quantum dot fluorescing in the NIR-II region.

8. The method of claim 7, wherein the quantum dot is selected from the group consisting of $Ag_2S$, PbS and $Ag_2Se$.

9. The method of claim 8, wherein the quantum dot is $Ag_2S$ having a diameter between 2 and 50 nm.

10. The method of claim 1, wherein the solubilized nanostructures further comprise fluorophores that are organic small molecules fluorescing in the NIR-II region.

11. The method of claim 10, wherein the organic small molecules are IR-1051 (6-Chlor-2-[2-[3-[(6-chlor-1-ethyl-2H-benzo[cd]indol-2-yliden)-ethyliden]-2-phenyl-1-cyclopenten-1-yl]-ethenyl]-1-ethyl-benzo[cd]indolium tetrafluoroborate), IR-26 (4-(7-(2-phenyl-4H-1-benzothiopyran-4-ylidene)-4-chloro-3,5-trimethylene-1,3,5-heptatrienyl)-2-phenyl-1-benzothiopyrylium perchlorate), and IR-1061 (4-[2[2-Chloro-3-[(2,6-diphenyl-4H-thiopyran-4-ylidene) ethylidene]-1-cyclohexen-1-yl]ethenyl]-2,6-diphenylthiopyrylium tetrafluoroborate).

12. The method of claim 1, wherein imaging is done at a penetration depth between 5 mm-1 cm.

13. The method of claim 12, wherein the solubilized nanostructure is a carbon nanostructure.

* * * * *